(12) United States Patent
Karlsson et al.

(10) Patent No.: US 7,390,650 B2
(45) Date of Patent: Jun. 24, 2008

(54) SYSTEM AND METHOD FOR OBTAINING AND MAINTAINING HIGH-RESISTANCE SEALS IN PATCH CLAMP RECORDINGS

(75) Inventors: Mattias Karlsson, Göteborg (SE); Owe Orwar, Hovås (SE); Daniel T. Chiu, Seattle, WA (US); Jon Sinclair, Göteborg (SE); Kent Jardemark, Gothenburg (SE); Jessica Olofsson, Gothenburg (SE); Johan Pihl, Gothenburg (SE); Cecilia Farre, Vastra Frolulnda (SE)

(73) Assignee: Cellectricon AB, Gothenburg (SE)

( * ) Notice: Subject to any disclaimer, the term of this patent is extended or adjusted under 35 U.S.C. 154(b) by 677 days.

(21) Appl. No.: 10/645,834

(22) Filed: Aug. 20, 2003

(65) Prior Publication Data
US 2004/0110307 A1    Jun. 10, 2004

Related U.S. Application Data

(60) Provisional application No. 60/404,886, filed on Aug. 21, 2002.

(51) Int. Cl.
   *C12M 1/34* (2006.01)
   *G01N 27/327* (2006.01)
(52) U.S. Cl. ............ 435/287.1; 435/285.2; 435/288.5; 422/82.02; 204/403.01
(58) Field of Classification Search ............ 435/285.2, 435/287.1
   See application file for complete search history.

(56) References Cited

U.S. PATENT DOCUMENTS

| | | | |
|---|---|---|---|
| 5,137,817 A | 8/1992 | Busta et al. | 435/173 |
| 5,449,492 A | 9/1995 | Krishtal | 422/64 |
| 5,501,662 A | 3/1996 | Hofmann | 604/20 |
| 5,597,699 A | 1/1997 | Lanzara | 435/7.21 |
| 6,193,647 B1 | 2/2001 | Beebe et al. | 600/33 |
| 6,242,209 B1 | 6/2001 | Ransom et al. | 435/29 |
| 6,368,851 B1 | 4/2002 | Baumann et al. | 435/285.2 |
| 6,470,226 B1 | 10/2002 | Olesen et al. | 700/56 |
| 6,686,193 B2 * | 2/2004 | Maher et al. | 435/285.2 |
| 2001/0029320 A1 | 10/2001 | Trumbull et al. | 600/300 |

(Continued)

FOREIGN PATENT DOCUMENTS

DE    199 36 302 A 1    2/2001

(Continued)

OTHER PUBLICATIONS

Sinclair, et al. "A Cell-Based Bar Code Reader for High-Throughput Screening of Ion Channel-Ligand Interactions", Anal. Chem. 2002, 74, 6133-6138.

(Continued)

*Primary Examiner*—William H Beisner
(74) *Attorney, Agent, or Firm*—David G. Conlin; Jeffrey L. Kopacz; Edwards Angell Palmer & Dodge LLP

(57) ABSTRACT

The invention provides a system, system components, and a method for rapidly obtaining and stably maintaining a cell in optimal contact with the cell-contacting surface of a sensor in a cell-based biosensor. In one aspect, the system maximizes the seal between a whole cell and the cell-contact surface of a patch clamp micropipette, maximizing the efficiency of a whole cell patch clamp recording.

18 Claims, 15 Drawing Sheets

U.S. PATENT DOCUMENTS

| | | |
|---|---|---|
| 2002/0074227 A1 | 6/2002 | Nisch et al. .................. 204/450 |
| 2002/0076689 A1 | 6/2002 | Farb et al. ....................... 435/4 |
| 2002/0146822 A1 | 10/2002 | Takayama et al. ........... 435/375 |
| 2003/0009112 A1 | 1/2003 | Hammerle et al. ........... 600/547 |
| 2003/0022268 A1 | 1/2003 | Lepple-Wienhues ......... 435/29 |
| 2003/0129581 A1* | 7/2003 | Owen et al. .................... 435/4 |
| 2003/0153067 A1 | 8/2003 | Stett et al. ................ 435/285.2 |
| 2004/0182707 A1* | 9/2004 | Jardemark et al. .......... 204/451 |
| 2005/0009171 A1 | 1/2005 | Fertig et al. |

FOREIGN PATENT DOCUMENTS

| | | |
|---|---|---|
| GB | 2 371 626 A | 7/2002 |
| WO | WO 90/04645 | 3/1990 |
| WO | WO 94/20841 | 9/1994 |
| WO | WO 96/10170 | 4/1996 |
| WO | WO 97/05922 | 2/1997 |
| WO | WO 99/24110 | 5/1999 |
| WO | WP-99/66329 A1 | 12/1999 |
| WO | WO 00/20554 | 4/2000 |
| WO | WO-01/25769 A2 | 4/2001 |
| WO | WO-02/04943 A2 | 1/2002 |
| WO | WO 0203058 A2 * | 1/2002 |
| WO | WO-02/24862 A2 | 3/2002 |
| WO | WO-02/24862 A3 | 3/2002 |
| WO | WO-02/065092 A2 | 8/2002 |
| WO | WO-03/089564 A1 | 10/2003 |

OTHER PUBLICATIONS

Farre, et al., "Screening of Ion Channel Receptor Agonists Using Capillary Electrophoresis-Patch Clamp Detection with Resensitized Detector Cells", Anal. Chem. 2001, 73, 1228-1233.

Stromberg, et al., "Microfluidic Device for Combinatorial Fusion of Liposomes and Cells", Anal Chem. 2001, 73, 126-130.

Jardemark, et al., "Screening of Receptor Antagonists Using Agonist-Activated Patch Clamp Detection in Chemical Separations", Anal. Chem. 1998, 70, 2468-2474.

Fishman, et al., "Cell-to-Cell Scanning in Capillary Electrophoresis", Analytical Chemistry, vol. 68, No. 7, Apr. 1, 1996, 1181-1186.

Fishman, et al., "Identification of receptor ligands and receptor subtypes using antagonists in a capillary electrophoresis single-cell biosensor separation system", Proc. Natl. Acad. Sci. USA, vol. 92, pp. 7877-7881, Aug. 1995.

Klemic, et al., "Micromolded PDMS planar electrode allows patch clamp electrical recordings from cells", Biosensors and Bioelectronics 17 (2002) 597-604.

Fertig, et al., "Whole Cell Patch Clamp Recording Performed on Plana Glass Chip", Biophysical Journal, vol. 82, Jun. 2002, 3056-3062.

Hamill, et al., "Improved Patch-Clamp Techniques for High-Resolution Current Recording from Cells and Cell-Free Membrane Patches", Pflugers Archiv (1981) 391:85, pp. 100-104.

* cited by examiner

FIG. 2A
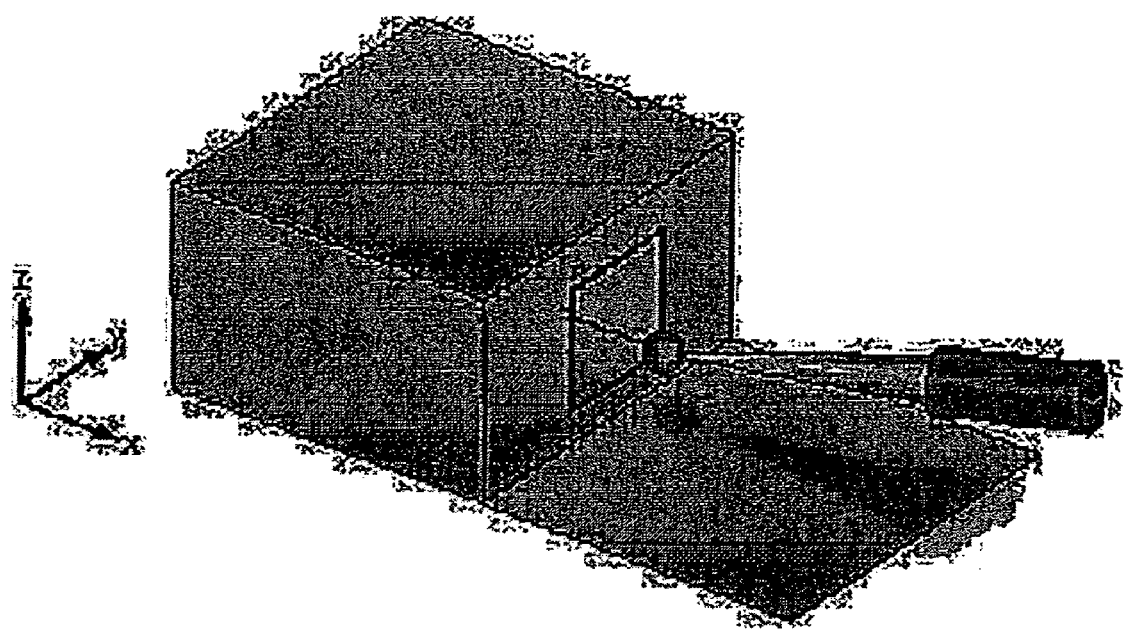
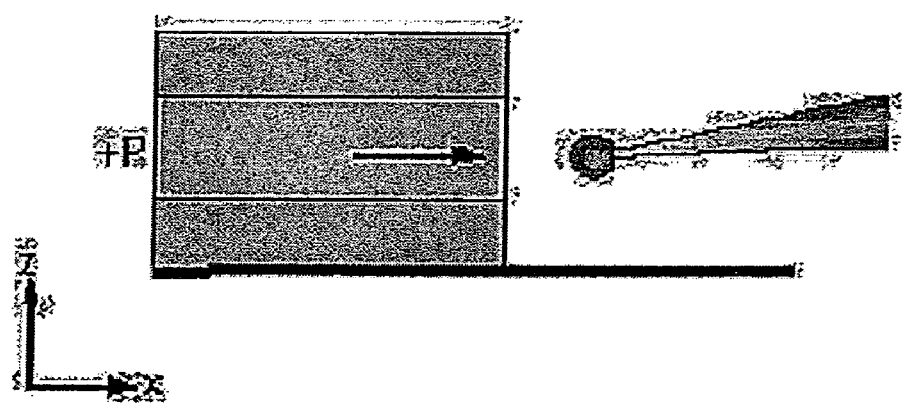
FIG. 2B

FIGS. 3A-C
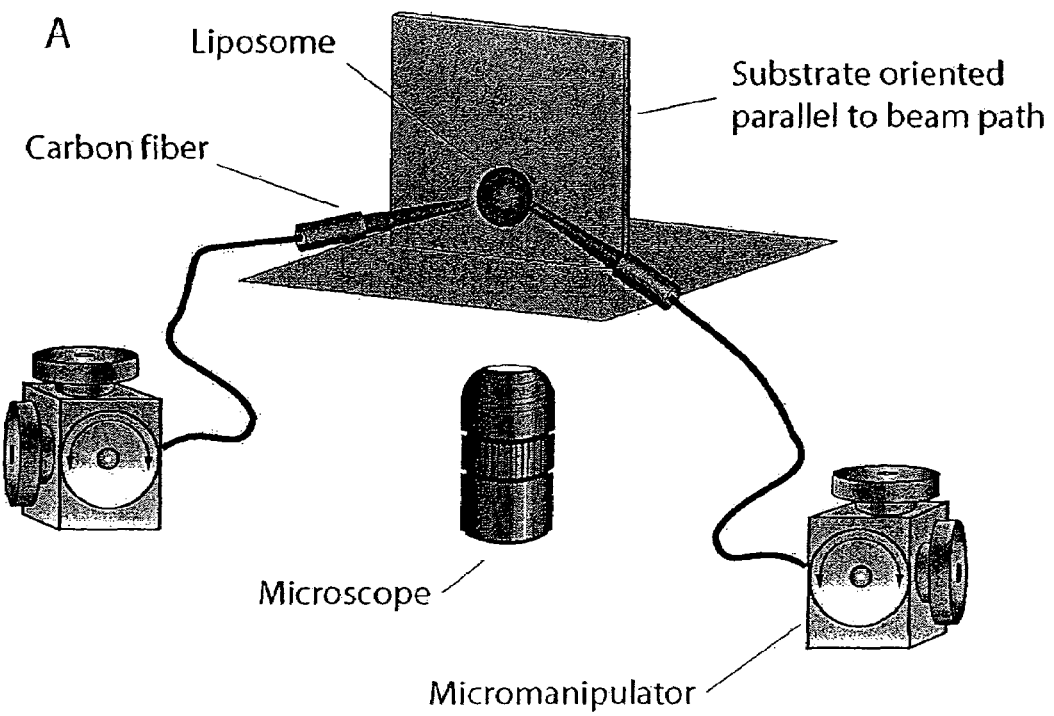
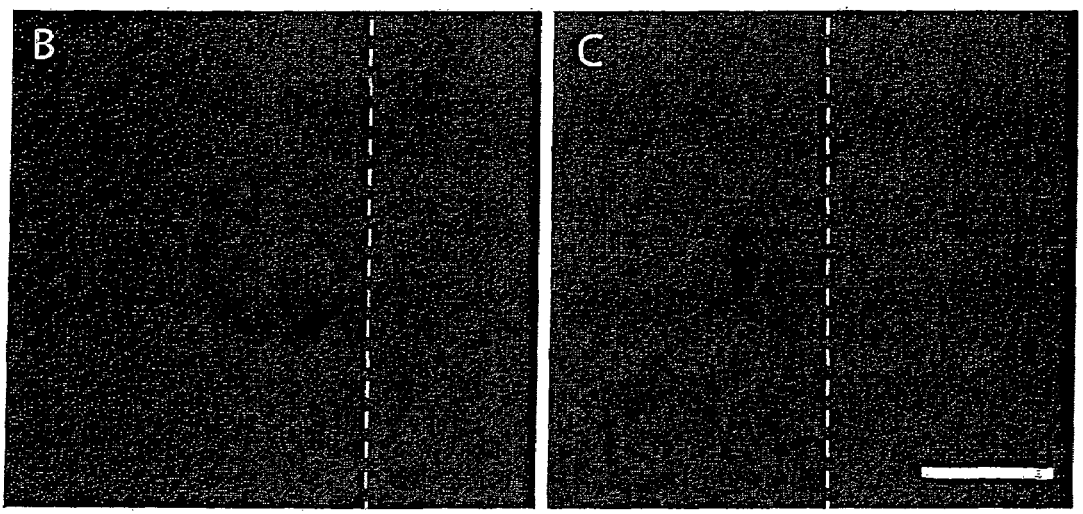

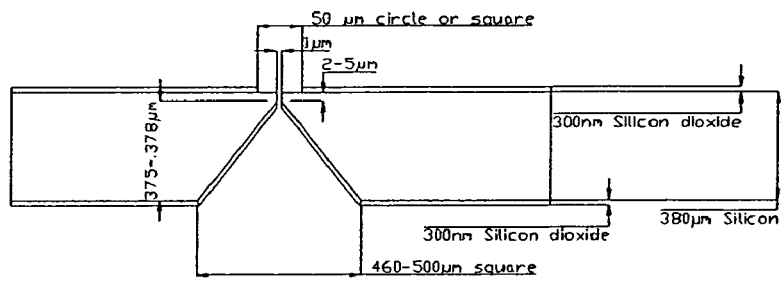
FIG. 4I
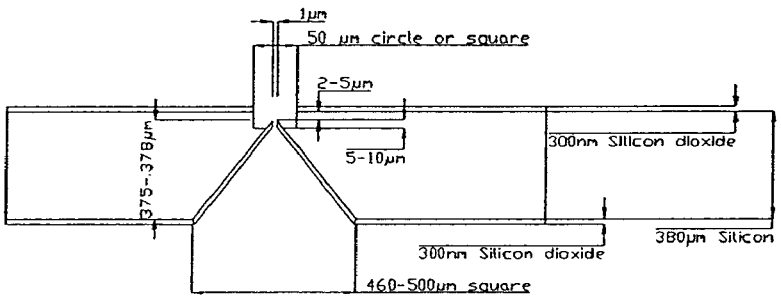
FIG. 4J
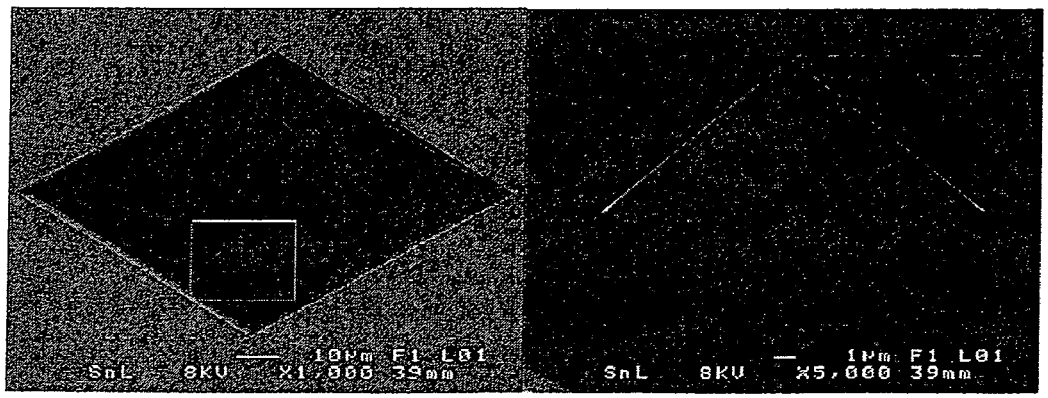
FIG. 4K
FIG. 4L

FIGS. 5A-D
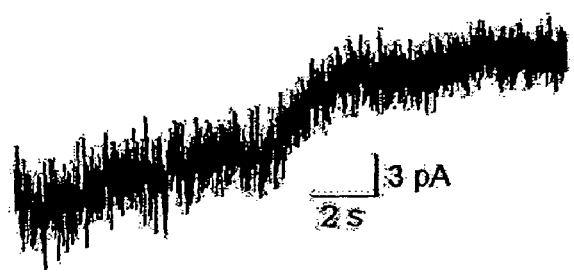
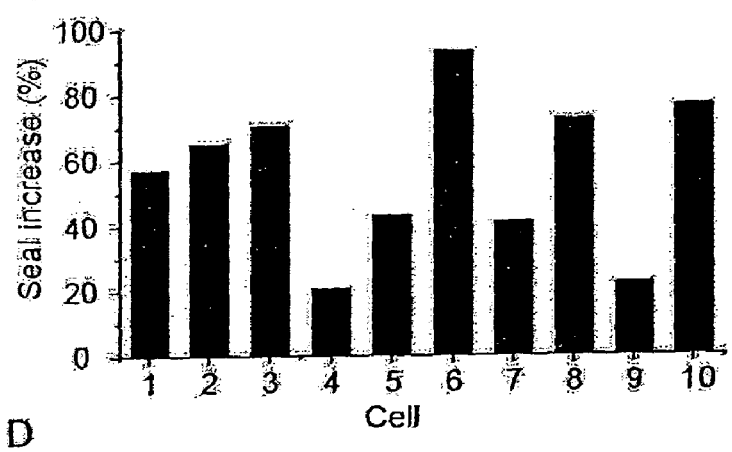
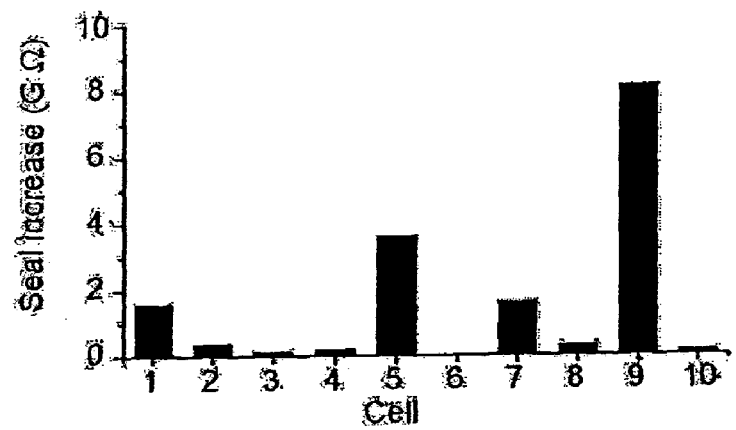

FIG. 10A
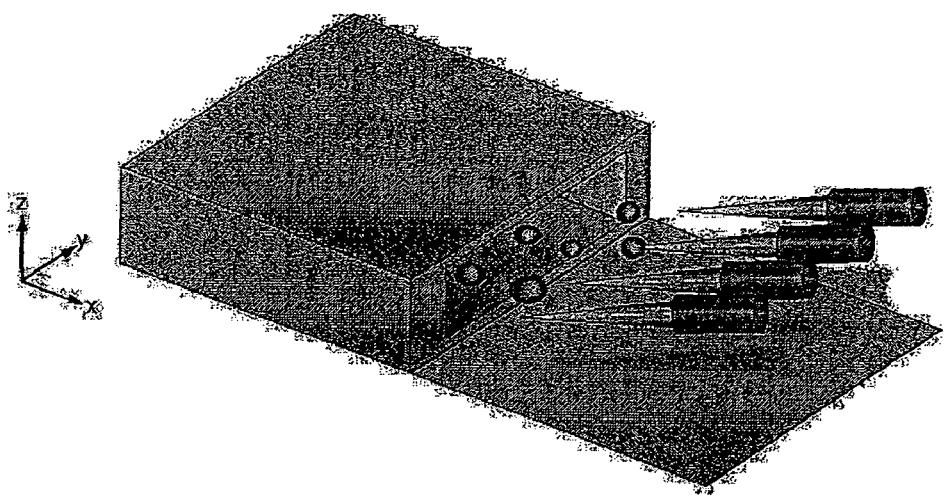
FIG. 10B
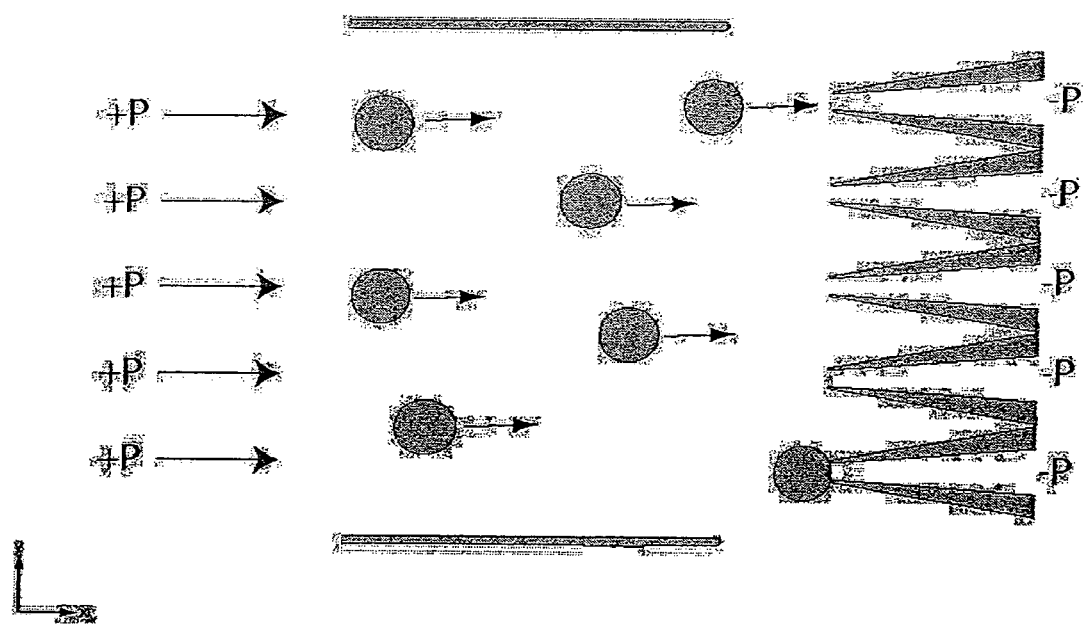
Fig. 10

SYSTEM AND METHOD FOR OBTAINING AND MAINTAINING HIGH-RESISTANCE SEALS IN PATCH CLAMP RECORDINGS

RELATED APPLICATIONS

This application claims priority under 35 U.S.C. § 119(e) to U.S. Provisional Application Ser. No. 60/404,886, filed Aug. 21, 2002, the entirety of which is incorporated by reference herein.

FIELD OF THE INVENTION

The invention relates to a system and method for obtaining and/or maintaining a high electrical resistance seal between a cell and an opening in an insulating surface that couples the cell to an electrode compartment for patch clamp recording. In one aspect, the surface is the opening of a patch clamp micropipette. In another aspect, the opening is an aperture in an on-chip patch clamp device.

BACKGROUND OF THE INVENTION

Ion-channels are important therapeutic targets. Neuronal communication, heart function, and memory all critically rely upon the function of ligand-gated and voltage-gated ion-channels. In addition, a broad range of chronic and acute pathophysiological states in many organs such as the heart, gastrointestinal tract, and brain involve ion channels. Indeed, many existing drugs bind receptors directly or indirectly connected to ion-channels. For example, anti-psychotic drugs interact with receptors involved in dopaminergic, serotonergic, cholinergic and glutamatergic neurotransmission.

Voltage clamp methods are superior to any other technology for measuring ion channel activity in cells (see, e.g., Neher and Sakmann, *Nature* 260: 799-802; Hamill, et al., 1981, *Pflugers Arch* 391: 85-100; Sakmann and Neher, 1983, In *Single-Channel Recording* pp. 37-52, Eds. B. Sakmann and E. Neher. New York and London, Plenum Press).

Among voltage clamp techniques, patch clamp is most suitable for measuring currents in the pA range (see e.g. Neher and Sakmann, 1976, supra; Hamill, et al., 1981, supra; Sakmann and Neher, 1983, supra). Variations of patch clamp techniques can be utilized such as whole-cell recording, inside-out recording, outside-out recording, and perforated patch recording as are known in the art.

In whole-cell recording, the cell membrane covering the electrode tip is believed to be ruptured by suction in order to establish an electrical connection (and a chemical pathway) between the cell interior and the electrode solution. Because electrode solution is in great excess compared to the amount of cytosol in the cell (about 10 μl vs. about 1 pl), changing ionic species in the electrode solution will create concentration gradients across the cell membrane, providing a means to control the direction and magnitude of the transmembrane ionic flow for a given receptor/ion-channel complex.

In inside-out and outside-out patch clamp configurations, the cytosolic environment is lost by excision of a membrane patch from the entire cell (see, e.g., Neher and Sakmann, 1976, supra; Sakmann and Neher, 1983, supra). To obtain an excision of a patch in both the inside-out and the outside-out configurations, the cells are preferably attached to the bottom of the cell dish or recording chamber. In the case of acutely isolated cells, for example, poly-L-lysine can be used to fix the cells to the bottom of the chamber.

The inside-out configuration allows exposure of the cytosolic side of the membrane to solution in the recording chamber. It is therefore a method of choice for studying gating properties of second-messenger activated ion-channels at the single-channel level. Thus, the effects of cytosolic signaling molecules or enzymatic activity on ion-channel function can be studied by means of this configuration. The outside out configuration, on the other hand, allows exposure of the extracellular side of the patch. It can therefore be used to monitor the activity of ligand-gated or receptor-operated ion-channels.

One frequently used modification of the whole-cell configuration, the perforated patch mode also can be used (see, e.g., as described in Pusch and Neher, 1988, supra). In this technique, holes are selectively made in the cell membrane using a pore-building protein, such as amphotericin or nystatin (see, e.g., Akaike et al., 1994, *Jpn. J. Physiol.* 44: 433-473; Falke, et al., 1989, *FEBS Lett.* 251: 167; Bolard, et al., 1991, *Biochemistry* 30: 5707-5715) to create increased conductivity across the patched cell membrane without the loss of intracellular signaling molecules. In addition to measuring ion currents across ion channels at constant membrane potential, the patch clamp technique can be used to measure membrane voltage at a known constant or time-varying current. And in another aspect, the patch clamp technique can be used to monitor capacitance changes in cell membranes by providing a cell-based biosensor in the open volume reservoir and measuring impedance of the membrane across the membrane of the biosensor in an AC mode.

Patch clamp is traditionally performed using tapered glass micropipettes. However, recently there has been considerable effort in developing patch clamp devices on solid substrates such as silicon chips. Typically, these substrates have been equipped with one or several openings for placement and sealing of cells equivalent to the opening of a traditional patch clamp electrode. For example, Klemic, et al., in WO 01/59447, describe a planar patch clamp electrode array comprising a plurality of electrodes for performing patch clamp recordings on a plurality of patch-clamped cells.

Low noise levels provide better signal-to-noise ratios in patch clamp recordings. The low noise property of patch clamp is achieved by tightly sealing a glass microelectrode or patch clamp pipette onto the plasma membrane of an intact cell thereby producing an isolated patch. The electrical resistance between the pipette and the plasma membrane is critical to minimize background noise and should be in excess of $10^9$ ohm to form a "giga seal". The exact mechanism behind the formation of the "giga seal" is debated, but it has been suggested that various interactions such as salt-bridges, electrostatic interactions, and van der Waal forces mediate the interaction between the glass surface of the pipette and the hydrophilic heads in the lipid layer of the cell membrane (see, e.g., Corey and Stevens, 1983, In *Single-Channel Recording*, pp. 53-68, Eds. B. Sakmann and E. Neher. New York and London, Plenum Press). Under optimal conditions, single-channel currents in the higher femto-ampere ($10^{-15}$ A) range can be resolved. Strategies to decrease noise (e.g., such as caused by a bad seal between the electrode and the cell) to facilitate formation of GΩ-seals include, but are not limited to, fire polishing of the glass electrode or treating the surface of the glass electrode using agents such as sigmacote. Dielectric noise and capacitive-resistive charging noise also can be decreased by selecting an expedient electrode/pipette geometry, using quartz glass, and by coating of the glass surface of the pipette with Sylgard® (silicone, PDMS) in order to decrease the capacitance of the pipette as much as possible.

However, it has proven difficult to obtain and maintain cells attached to both solid substrate chips and traditional path clamp micropipettes with good electrical sealing properties.

Typical success rates for obtaining a whole cell-recording configuration with both techniques is about 50%. Further, the time periods during which cells can be held in a satisfactory position relative to a patch clamp micropipette to obtain a recording rarely exceeds 20 minutes.

BRIEF DESCRIPTION OF THE FIGURES

The objects and features of the invention can be better understood with reference to the following detailed description and accompanying drawings. The Figures are not drawn to scale. In the Figures below, "P" refers to pressure, while "V" refers to voltage.

FIGS. 2A and B are schematic diagrams illustrating the stabilization of a patch clamp seal under fluid flow due to a resulting drag force. FIG. 2A is a perspective view of a cell-based biosensor comprising a patch clamp micropipette positioning a cell in proximity to a source of fluid flow. FIG. 2B shows a side view of the cell-based biosensor shown in FIG. 2A. The arrow indicates direction of fluid flow through the fluid flow source, created by a positive pressure, P, at a fluid source.

FIGS. 3A-C show a method for maximizing seal resistance according to one aspect of the invention. FIG. 3A is a schematic diagram demonstrating a device for measuring the degree of contact between a coverslip and a liposome positioned in proximity to the treated surface of the coverslip. FIGS. 3A and B are fluorescence micrographs showing the enhanced contact between a giant unlilamellar vesicle and the surface of a coverslip before (FIG. 3B) and after (FIG. 3C) hydrolyzing the surface, illustrating the importance of surface chemistry in patch clamp experiments.

FIGS. 4A-J-illustrate a fabrication procedure used to make a protruded opening in the surface of an on-chip patch clamp device. FIG. 4K is a perspective view which shows the opening of a cell chamber or well for receiving a cell in an on-chip patch clamp device. The base of the cell chamber is in communication with one or more electrodes (not shown). FIG. 4L shows a pyramidal protrusion fabricated at the base of the cell chamber according to the process shown in FIGS. 4A-J. The protrusion maximizes the electrical resistance of the seal formed between the cell and the opening of the cell chamber.

FIGS. 5A-D show a patch clamp recording and analysis of 10 cells showing the increase in seal resistance under fluid flow. FIGS. 5A and 5B are current traces illustrating the decrease in leakage current typically observed as a cell is positioned in a flow path. FIG. 5A shows the increase in electrical resistance observed for a cell which has already been sealed against a patch clamp opening when the cell is exposed to a fluid stream. The seal resistance increase is from about 2.1 GΩ to 3.7 GΩ. FIG. 5B shows that for a weak seal, i.e., where the cell is in proximity to a patch clamp opening, but not tightly sealed against it, the seal resistance increases from 50 MΩ to 240 MΩ. FIG. 5C shows that the average seal resistance for ten cells increases by about 56%. FIG. 5D shows an average increase of 1.6 GΩ.

FIG. 7A shows a cell in proximity to an opening which is not sealed against the opening and which is not exposed to fluid flow. FIG. 7B, shows the use of pressure or an electrical field to create a seal between the cell and the opening. FIG. 7C shows the use of a fluid stream (indicated by the arrow) from a fluid source (e.g., such as a microchannel) to create a seal between a cell and opening. FIG. 7D shows the use of pressure or an electrical field to create a seal between the cell and opening, together with the use of fluid flow to increase electrical resistance at the seal.

FIGS. 10A and B are different views of a cell-based biosensor for obtaining patch clamp recordings in which cells automatically positioned at a plurality of micropipette tip openings are moving in a stream at an angle to a plane containing the plurality of openings. FIG. 10A is a perspective view. FIG. 10B is a top planar view through a cross section of the system shown in FIG. 10A. The arrows show the direction of cell movement in fluid flowing from a fluid source in the direction of the plurality of micropipette tip openings.

SUMMARY OF THE INVENTION

Figure 1A:
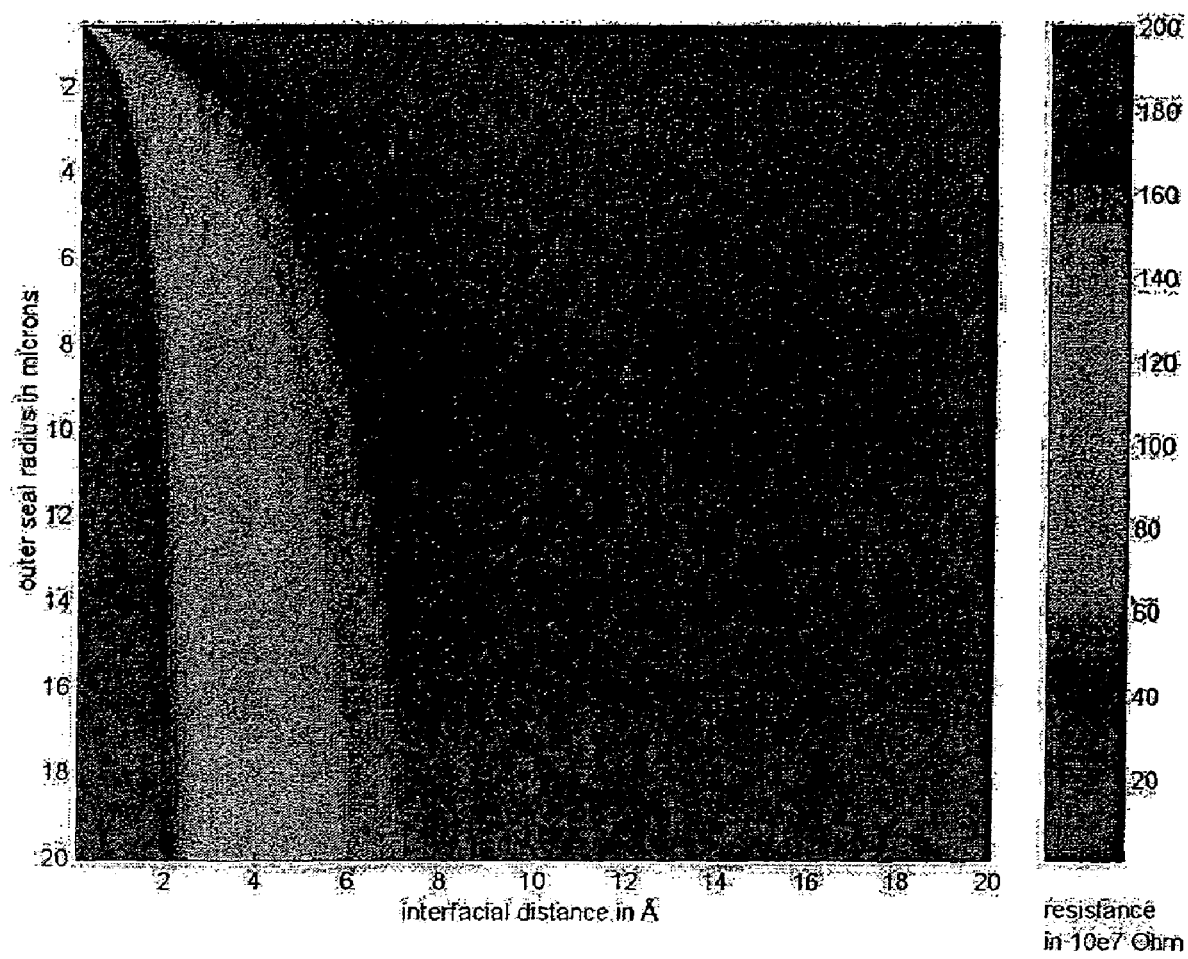
FIGS. 1A and B illustrate methods according to the invention for maximizing seal resistance during a patch clamp recording by optimizing the geometry at an opening separating a cell or portion thereof from an electrode for patch clamp recording. In both FIGS. 1A and B, the radius of the opening is 0.5 μm. The diagrams show the resistance of the seal (given as a greyscale) as a function of the interfacial distance and the extension of the seal (i.e., length in axial direction in A and radius of contact zone in B).

The invention provides systems and methods for generating a high electrical resistance seal between a cell and a surface defining an opening that couples the cell to an electrode compartment. When the cell membrane is sealed against the surface, the cell membrane is in electrical communication with an electrode within the electrode compartment.

In one aspect, the invention provides modified surfaces for optimising the seals between a cell and surface which couples the cell to an electrode compartment. For example, in one aspect, the surface is nonplanar and creates a stress on the cell that creates a tighter seal against the surface. Preferably, the surface is protruded. The surface defining the opening can be part of an on chip patch clamp device, such as an aperture patch clamp array device, or can be the tip of a patch clamp micropipette. Preferably, the electrical resistance generated when the seal is formed is at least 100 Mohm, at least 1 Gohm, at least 10 Gohm, or at least 100 Gohm.

The invention also provides an on chip patch clamp device comprising a cell chamber comprising a non-planar element for maximizing the electrical resistance of a seal formed between a cell and opening of the cell chamber. In this aspect, the cell chamber defines the electrode compartment, comprising one or more electrical elements at the base of the chamber and an electrolyte solution separating the cell and preventing direct contact between the cell and one or more electrical elements. In one aspect, the non-planar element in the cell chamber is pyramidal-shaped, conical, elliptical, or toroidal. In another aspect, the nonplanar element comprises a recession for receiving the cell. Preferably, the on chip patch clamp device is an array device comprising a plurality of cell chambers, and at least one of the cell chambers comprises a non-planar element. More preferably, substantially all of the cell chambers comprise non-planar elements.

In another aspect of the invention, the surface defining the opening which couples the cell membrane to the electrode compartment is modified to provide a surface chemistry that optimises the formation of a high electrical resistance seal at the surface. Preferably, the surface comprises hydrophilic molecules or is treated to be rendered hydrophilic. For example, the surface can be exposed to chemical washing, using an RCA procedure or chemical agents, such as peroxides, ammonia, or nitric acid.

In one preferred embodiment, a surface so treated is the surface of an on chip patch clamp device, such as a patch clamp array device. Preferably, the electrical resistance generated when a seal is formed at such a surface is at least 100 Mohm, at least 1 Gohm, at least 10 Gohm, or at least 100 Gohm.

The invention also provides systems (e.g., microfluidic chips or biosensors) comprising substrates that include one or more cell chambers for receiving one or more cells. The cell chambers may form electrode compartments (e.g., as in an on chip patch clamp device) or may receive cells for positioning the cells in proximity to electrode compartments (e.g., such as provided by patch clamp micropipettes). The substrate may comprise one more microchannels for delivering cells to appropriate cell chambers. One or more of: pressure, optical tweezers, electroosmosis, dielectrophoresis, and ac or dc currents, may be used to route a cell from a microchannel to an appropriate cell chamber.

Preferably, the substrate comprises at least one fluid source for providing a fluid stream in proximity to one or more cells in the cell chamber(s). The fluid stream is used to establish and/or maintain a high electrical resistance seal between a cell and a surface defining an opening for separating the cell from an electrode compartment. In one aspect, the fluid stream is delivered through a microchannel which comprises an outlet which opens into the cell chamber. In another aspect, the substrate comprises a plurality of microchannels, each having an outlet for delivering fluid streams into a cell chamber. Preferably, the system comprises a fluid controlling mechanism for controlling hydrostatic pressure at one or more outlets. Hydrostatic pressure at one or more channels can be varied by a processor in communication with the system according to programmed instructions and/or in response to a feedback signal. In one aspect, hydrostatic pressure at each of the plurality of channels is different.

The system may further comprise a scanning mechanism for scanning the position of the cell chamber relative to the inlets of the channels and/or for scanning cells in the cell chamber relative to the inlets.

Preferably, the scanning mechanism is in communication with a processor and translation occurs in response to instructions from the processor (e.g., programmed instructions or instructions generated as a result of a feedback signal). In one aspect, the processor controls one or more of: the rate of scanning, the direction of scanning, acceleration of scanning, and number of scans.

Preferably, aqueous streams exiting from the at least two adjacent channels are collimated and laminar within the open volume. However, the system can comprise sets of channels (at least two adjacent channels) wherein at least one set delivers collimated laminar streams, while at least one other set delivers non-collimated, non-laminar streams. In one aspect, the streams flow at different velocities. Fluid can be delivered from the channels to the chamber by a number of different methods, including by electrophoresis and/or by electroosmosis and/or by pumping.

In one aspect, the longitudinal axes of the channels are substantially parallel. The channels can be arranged in a linear array, in a two-dimensional array, or in a three-dimensional array, can comprise treatment chambers, sensor chambers, reservoirs, and/or waste channels, and can be interfaced with container(s) or multi-well plate(s). In one aspect, the system comprises at least one input channel for delivering at least one fluid stream into a cell chamber and at least one output or drain channel for removing fluid from the cell chamber. In another aspect, output channels can overly input channels (i.e., in a three-dimensional configuration). Preferably, the longitudinal axis of at least one output or drain channel is parallel, but lying in a different plane, relative to the longitudinal axis of at least one input channel. By applying a positive pressure to an input channel at the same time that a negative pressure is applied to an adjacent output or drain channel, a U-shaped fluid stream can be generated within the chamber. The U-shaped fluid streams can be used to create pressure against cells to position and/or seal cells against surfaces which couple the cells to an electrode compartment.

In one preferred aspect, one or more fluid streams are used to create a high electrical resistance seal between one or more cells in the cell chamber and one or more surfaces defining openings which separate the cell(s) from electrode compartment(s). For example, fluid streams are used to create high electrical resistance seals between cells and patch clamp micropipettes that are positioned in proximity to the cell chamber (either by moving the cell chamber, moving the micropipettes or by moving both the cell chamber and micropipettes). By controlling the direction of a fluid stream and pressure applied through the fluid stream, a seal with high electrical resistance (e.g., greater than 100 Mohm, and preferably, greater than 1 Gohm) is created.

The invention further provides a method for generating a high electrical resistance seal between a cell membrane and a surface defining an opening for coupling a cell to an electrode compartment. The method comprises exposing the cell to a fluid stream to push the cell against the surface and to obtain a high electrical resistance seal at the surface. Preferably, the seal is maintained for a prolonged period of time, i.e., greater than about 20 minutes, greater than about 30 minutes, greater than about an hour, greater than about 2 hours, or greater than about 5 hours.

The seal may be enhanced by providing a modified surface as described above (e.g., by providing a non-planar or protruded surface, and/or by rendering the surface hydrophilic). Suction or one or more voltages may be applied at the opening to further maximize the electrical resistance of the seal.

In one preferred aspect, the seal created establishes electrical communication between a cell membrane and an electrode in the electrode compartment, enabling electrical properties of the cell membrane to be measured. In one aspect, the method is used to obtain patch clamp recordings. Electrical properties recorded may be used to monitor one or more cellular responses and/or cellular properties including, but not limited to: cell surface area, cell membrane stretching, ion-channel permeability, release of internal vesicles from a cell, retrieval of vesicles from a cell membrane, levels of intracellular calcium, ion-channel induced electrical properties (e.g., current, voltage, membrane capacitance, and the like), or viability.

DETAILED DESCRIPTION

The invention provides a system, system components, and a method for rapidly obtaining and stably maintaining a cell membrane in optimal contact with the opening of a surface which couples a cell membrane to one or more electrodes for recording electrical properties of the cell, such that the cell is in electrical communication with the one or more electrodes. In one aspect, the surface is the opening of a patch clamp micropipette. In another aspect, the opening is the opening of a cell chamber in an on-chip patch clamp device, such as a patch clamp array device. Preferably, an electrolyte solution separates the cell from the one or more electrodes.

The invention further provides a system for maximizing the electrical resistance of a seal between a cell membrane, and the opening of a surface separating the cell membrane from an electrode compartment, maximizing the electrical resistance of a seal between the cell membrane and the opening. The invention also provides a method for providing an optimal configuration at the opening by providing one or more of: an optimal geometry and/or surface topography at the surface defining the opening; optimal surface chemistry at the surface defining the opening (e.g., providing hydrophilic groups at the surface); and fluid flow in proximity to a cell membrane positioned in proximity to the opening.

The systems and methods of the present invention may be used for techniques such as internal perfusion of oocytes, patch clamp electrophysiology, brain slice recording, receptor-ligand interactions on cell surfaces, calcium imaging studies, confocal microscopy, and in vivo microdialysis, for example. The system of the present invention may also be used to measure properties of ligand-gated ion channels, voltage-gated ion channels, G-protein coupled receptors, activities across a synapse, molecular transporters, cell-to-cell interactions and ion pumps, and to screen for modulators (agonists or antagonists) of these biomolecules.

Definitions

The following definitions are provided for specific terms which are used in the following written description.

As used in the specification and claims, the singular form "a", "an" and "the" include plural references unless the context clearly dictates otherwise. For example, the term "an opening" includes a plurality of openings. The term "an ion-channel" includes a plurality of ion channels. The term "an opening" or "the opening" can refer to a plurality of openings.

As used herein, a "patch clamp device" is a device suitable for obtaining patch clamp recordings. Generally, such a device comprises an insulating surface for separating a cell membrane from an electrode. The surface comprises an opening that couples the cell to the electrode through an electrolyte solution in a lumen defining the opening, such that the cell is in electrical communication with the electrode (e.g., exposed to an electrical field created by the electrode and capable of transmitting an electrical signal, such as a current or voltage, back to the electrode). As used herein, "a patch clamp device" refers to both a traditional patch clamp apparatus comprising a patch clamp micropipette which typically comprises an internal electrode, or an on-chip device, such as a patch clamp array device. In an "on-chip device", the insulating surface is generally fabricated in the form of a wafer or chip comprising a plurality of cell chambers or wells, each for receiving a cell. The base of a cell chamber comprises an electrical contact zone associated with one or more electrodes, while the opening of the chamber receives the cell. The cell chamber, like the micropipette of a traditional patch clamp device, is filled with an electrolyte solution for coupling the cell to an electrode, such that the cell is in communication with the electrode(s).

As used herein, the term "electrode" refers to a device that transmits or conducts electric signals.

As used herein, the term "electrolyte solution", refers to the solution within a cell chamber of a patch clamp array device or within a micropipette. The specific electrode solution used for measuring ionic current through a biological membrane of a cell is usually chosen so that it is similar to the intracellular solution of the cell. The bath solution and the electrode solution are typically chosen to be different when measuring the ionic current through a biological membrane of a cell; however, they may be the same.

As used herein, the term "bath solution" refers to the solution or medium surrounding the cell outside of a cell chamber or outside of a patch clamp micropipette. Preferably, a bath solution used for measuring the ionic current through a biological membrane of a cell is usually chosen so that it is similar to the external ionic environment that the cell is exposed to in vivo.

As used herein, the term "opening" refers to any aperture or orifice, such as a hole, gap or slit. The opening can take any shape or form; for example, it may be substantially elliptical, circular, square, or polyhedral. Openings used in patch clamp systems described herein range in size from about 0.1 micron to about 100 microns. However openings can range from at least about 0.01 µm, at least about 0.05 µm, at least about 0.1 µm, at least about 10 µm, at least about 15 µm, at least about 20 µm, at least about 50 µm, at least about 75 µm, or at least about 100 µm.

As used herein a "surface defining an opening" refers to a surface which includes an opening and which couples a cell to an electrode compartment. Typically, a surface defining an opening refers to that portion of the surface in contact with a cell membrane (e.g., such as the rim of a micropipette and the inner surface of the micropipette tip which contacts the cell membrane as a seal is formed, or in the case of an on-chip device, the rim of a cell chamber and the portions of the walls of the cell chamber which contact the cell when it is sealed against the cell chamber).

As used herein, "an electrode compartment" refers to one or more electrodes and lumen comprising an electrolyte solution which couples the one or more electrodes to a surface with an opening, to enable it to generate an electrical field at the opening or to receive electrical signals, such as current or voltage, for recording.

As used herein, a "cell chamber" generally refers to a chamber, well, depression or reservoir in a substrate for receiving one or more cells. In the context of a cell-based biosensor adapted for a traditional patch clamp device, a cell chamber is a chamber for receiving and positioning a cell in proximity to a patch clamp micropipette. The chamber is generally open volume (i.e., at least partially uncovered) and comprises bath solution. In the context of an on-chip patch clamp device, the chamber is generally adapted for receiving a single cell and comprises one or more electrodes at the base of the chamber. The chamber is preferably designed in a way that restricts the motion of a cell received in the chamber and comprises electrolyte solution for maintaining the cell in electrical communication with the electrodes at the base of the chamber.

As used herein, the term "cell membrane" refers to a lipid bilayer surrounding a biological compartment, and includes the membranes of natural or artificial cells (e.g., such as liposomes), membrane vesicles or portions thereof. The term "cell membrane" encompasses an entire cell comprising such a membrane, a portion of a cell, an artificial cell, or a portion of an artificial cell.

As used herein, a "patch" recording refers to a recording in which the patch clamp device collects ionic current passing through a membrane patch sealed against the opening of a patch clamp device.

As used herein, a "whole-cell recording" refers to a set-up in which the membrane patch is ruptured, giving direct electrical access to a cell's interior.

As used herein, the term "glass" refers to any of a large class of materials that are typically made by silicates fusing with, but not limited to, boric oxide, aluminum oxide, or phosphorous pentoxide.

As used herein, the term "high electrical resistance seal" refers to a seal between cell membrane and the opening of a surface separating the cell from an electrode compartment, whose integrity is shown by a high electrical resistance, which is preferably, greater than about 100 M$\Omega$, greater than about 200 M$\Omega$, greater than about 300 M$\Omega$, greater than about 400 M$\Omega$, greater than about 500 M$\Omega$, greater than about 600 M$\Omega$, greater than about 700 M$\Omega$, greater than above 800 M$\Omega$, greater than about 900 M$\Omega$, greater than about 1 G$\Omega$, greater than about 1.2 G$\Omega$, greater than about 1.3 G$\Omega$, greater than about 1.4 G$\Omega$, greater than about 1.5 G$\Omega$, greater than about 1.6 G$\Omega$, greater than about 1.7 G$\Omega$, greater than about 1.8 G$\Omega$, greater than about 1.9 G$\Omega$, greater than about 2 G$\Omega$, greater than about 10, about 20, about 30, about 40, about 50, about 60, about 70, about 80, about 90, about 100, about 150, or 200 G$\Omega$.

As used herein, a "microchannel" refers to a groove in a substrate comprising two walls, a base, at least one inlet and at least one outlet. In one aspect, a microchannel also has a roof. The term "micro" does not imply a lower limit on size, and the term "microchannel" is generally used interchangeably with "channel". Preferably, a microchannel ranges in size from about 0.1 μm to about 1000 μM, more preferably ranging from, 1 μm to about 500 μm.

As used herein, the term "substantially separate aqueous streams" refers to collimated streams with laminar flow.

As used herein, the term "receptor" refers to a macromolecule capable of specifically interacting with a ligand molecule. Receptors may be associated with lipid bilayer membranes, such as cellular, golgi, or nuclear membranes, or may be present as free or associated molecules in a cell's cytoplasm or may be immobilized on a substrate.

As used herein, the term "in communication with" refers to the ability of a system or component of a system to receive signals or input data from another system or component of a system and to provide an output response in response to the input data. "Output" may be in the form of data or may be in the form of an action taken by the system or component of the system or a signal delivered by the system or component of the system (e.g., to a detector). For example, a cell in "electrical communication" with an electrode refers a cell which receives a signal from an electrode (such as a voltage, or current, etc) and which provides a response to the signal in the form of a measurable change in an electrical property (e.g., such as a current).

As used herein, a "substantially planar substrate comprising a nonplanar element for establishing electrical communication with a cell" refers to substrate which comprises an element whose surface is elevated or depressed relative to the surface of a substrate, wherein the element comprises at least two points that lie in different planes relative to the surface of the substantially planar substrate and relative to each other. For example, a "non-planar element" may be pyramidal shaped, toroidal shaped, in the form of a pipet tip affixed to a substantially planar surface, or comprise a plurality of stacked planar elements.

As used herein, "a measurable response" refers to a response which differs significantly from background as determined using controls appropriate for a given technique.

As used herein, a "recording" refers to collecting and/or storing data obtained from processed electrical signals, such as are obtained in patch clamp analysis.

Parameters for Creating High Electrical Resistance Seals in a Biosensor

The main building block of the cell membrane is a heterogeneous mixture of liquid crystalline lipids that forms a 5 nm thick cell-enveloping bilayer. The lipid membrane does not form a smooth surface, but a surface full of irregularities and protrusions.

The highly flexible lipid bilayer is stabilized by the cell cytoskeleton, which is a dynamic system of protein filaments. The combination of the flexible liquid crystalline bilayer and a stabilizing (but not static) cytoskeleton give cells unique properties of both flexibility and mechanical stability.

The lipid bilayer constantly undergoes entropically driven fluctuations. These fluctuations are generally restrained by the cytoskeleton, but can still have amplitudes on the order of 10 nm and wavelengths of ~0.5 μm. These fluctuations are effectively quenched by introduction of tension in the membrane.

On the outside of nearly all cells, a low-density coating of membrane bound and (re-)adsorbed glycoproteins and glycolipids is found. This coating, called the glycocalyx, has a thickness varying from some tens to several hundred nanometers. One of the main functions of the glycocalyx is to prevent too close contact with other cells.

Cells adhere to their natural substrates mainly through cell adhesion molecules mediating "key and lock forces". However, different forces of nonspecific character do play an important role in cell adhesion and particularly in the non-natural adhesion involved in sealing a cell to the opening of an insulating surface that couples the cell to an electrode for patch clamp recording. In a traditional patch clamp device, this situation is observed at the tip of a patch clamp micropipette. In an on-chip device, such as a patch clamp array device, this situation is observed at the opening of a cell chamber which holds a cell in position relative to an electrode backplate, generally, at the base of the chamber. Such non-specific forces, being of both repelling and attracting character, and exhibiting different dependences on the interfacial distance between the cell and the cell-contacting surface, together create a potential surface with one or several minima. Together with constraints due to the restricted deformability cells can tolerate, the appearance of an energy surface determines the interfacial distance and the extension and stability of the contact.

Repulsive forces due to compression of oligosaccharide chains in the glycocalyx of a cell membrane dominate the interaction at interfacial distances of 10-100 nm and have to be overcome if closer contact is to be achieved. Another repelling force that has to be overcome in order to establish close contact is the one deriving from the entropically driven fluctuations of the lipid membrane. Other forces relevant to consider at shorter distances are electrostatic double-layer forces, hydration forces and van der Waals forces. These forces are related to the chemical appearance of the surface defining the opening of the patch clamp and the material of the cell-substratum.

Since pure lipid vesicles seal to glass it is likely that the lipids alone are responsible for the formation of high resistance seals between the opening of an insulating surface separating a cell from an electrode compartment (e.g., electrolyte solution and one or more electrodes) and a cell.

For example, the nature of gigaseals formed with ordinary patch-clamp pipettes varies with the starting conditions. Some seals are formed spontaneously upon touching the cell surface with the pipette, presumably due to the presence of a "clean cell" uncontaminated by debris in the medium and an ideal pipette surface/geometry, but in most cases, the pressure inside the pipette has to be lowered so that lipid membrane is drawn into the pipette. For seals formed after lowering the pressure, the pipette-spanning dome of the membrane often is situated tenths of microns up in the pipette.

Figure 1B:
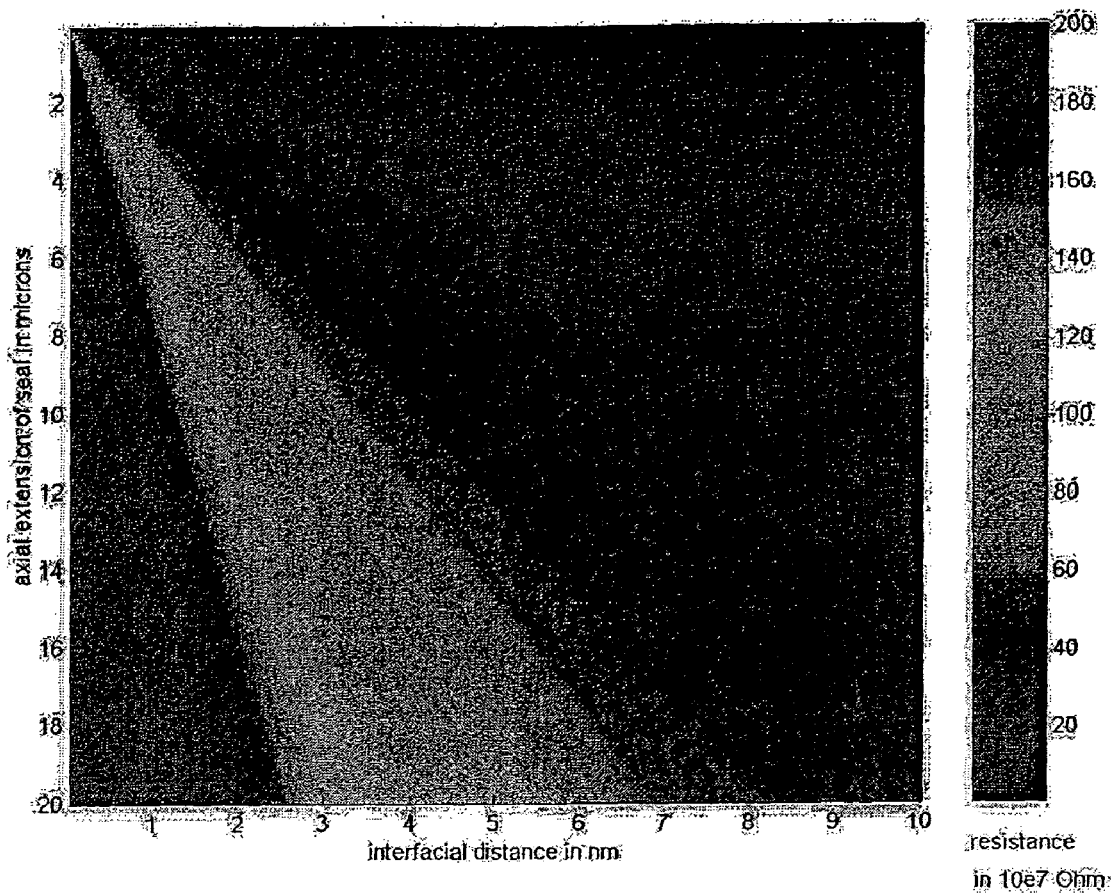

How small the interfacial distance has to be in order to obtain gigaseal resistances varies with the geometry of the seal and the extension of the contact area between the lipid membrane and the sealing surface (see, e.g., FIG. 1B). However, for all seals the cell-contacting surface, or sealing surface, has to be brought closer to the lipid membrane than is allowed when there are molecules extracellularly attached to the cell surface (e.g., such as cell receptors). At small separations, the van der Waals attraction becomes very strong and threatens to lock the cell, or parts of it, in an energy minima not possible to escape from. Thus, something is needed to maintain a proper distance—and in biologically "normal" situations, the glycocalyx and topographic roughness of a cell membrane at different points of the cell membrane allows for the formation of interfacial distances between other cell(s) at which the van der Waals attraction is weak or can be balanced by other forces. In order to obtain gigaseals between a cell membrane and the opening of a surface separating the cell membrane from an electrode compartment, these distance-keeping properties of the cell membrane have to be violated in an effective way.

(1) Geometrical Properties of a Surface Separating a Cell from an Electrode Compartment It is a discovery of the instant invention that a protruded surface defining an opening which separates a cell from an electrode compartment is important to minimize the separation distance between the opening and the cell membrane, and to increase electrical resistance at the contact point between the cell and the surface and opening The presence of molecules present on the cell surface prevents the close attachment of the cell membrane to the surface defining the opening. This is especially pronounced for surfaces that are either planar or recessed, because molecules attached extracellulary act as spacers that prevent close contact between the surface of the cell membrane and the surface defining the opening. In contrast, for a protruded surface defining an opening, the presence of molecules attached extracellularly is less critical in determining separation distance, because these molecules can be displaced much more easily in comparison with the other geometries.

This displacement is possible for a protruded surface defining an opening because: (1) the initial contact area between the surface defining the opening and cell membrane surface is very small; and (2) the local pressure (from suction or pressure on the cell membrane) and stress that can be applied to the cell surface is very high. In combination, these two effects cause the displacement of molecules attached extracellularly at the initial contact region between the cell membrane surface and the protruded surface defining the opening, thus dramatically reducing the separation distance between the two surfaces. This introduced pressure increases membrane tension that quenches entropically driven fluctuations of the lipid membrane and smoothes irregularities on the membrane surface.

Another important factor, illustrated in FIG. 1B, is the effect of the geometry of the surface defining the opening on the quality of the seal between a cell and the surface. For a given separation distance between the surface of the membrane and the surface defining the opening, a protruded surface defining an opening with a cylinder-like interior/exterior is superior for obtaining high resistance seals than a planar one. This can be illustrated for an insulating surface separating a cell membrane from an electrode compartment, in which current is delivered to the cell membrane from the electrode compartment. By dividing the path of the current into segments, it can be shown that for a protruded surface, each equally long path segment will contribute equally to the total seal resistance due to a constant cross-sectional area of the leaking current along the current path.

In contrast, a different phenomenon occurs when a cell is sealed against a planar surface comprising an opening. When current leaks through such a seal, it leaks out in a radial direction from the opening. In this case, the resistance contribution from each radial segment of the seal formed between the cell and the planar surface comprising the opening is inversely proportional to the radius of the segment. This means that leakage may increase along the current path and consequently, that current density will decrease, illustrating the inefficiency of the geometry.

The dependence of resistance on seal area (the contact between a micropipette surface) can also be seen in the equations used for the simulations presented in FIGS. 1A and B.

For planar geometries, the resistance R is calculated as $$R = \frac{1}{2\pi\sigma d} \cdot \ln(r_o/r_i)$$

where $\sigma$ is the conductivity of the electrolyte, d, the dimension of the interfacial cleft, $r_o$, the outer radius of the seal area and $r_i$, the inner radius of the seal area (i.e., the radius of the opening).

For cylindrical geometries, the resistance R is calculated as $$R = \frac{a}{[r^2\pi - (r-d)^2\pi]\sigma}$$

where α is the length of the seal in the axial direction of the pipette, r, the pipette inner radius, and d, the interfacial distance between the pipette inner/outer wall and the lipid membrane.

In the simulations, σ is set to 16 mS/cm.

(2) Chemical Surface Properties of the Surface Defining the Opening

FIG. 1A illustrates the importance of minimizing the distance between the cell membrane and the surface defining an opening which separates the cell membrane from an electrode compartment or, as holds for some geometries, the importance of increased t contact area between the cell membrane and the surface defining the opening.

In one aspect, therefore, the invention provides a method for maximizing seal resistance between a cell and such an opening, thereby to maximize the efficiency of patch clamp recordings. Empirically, it was found that the attractive interaction between a lipid membrane and a surface defining such an opening is maximized when the surface is made hydrophilic. The more hydrophilic the surface, the stronger is the attractive interaction. A strong attraction provides a larger contact area and a smaller separation distance between the two surfaces and results in higher seal resistance.

A strong attraction provides a larger contact area the surface interaction energies between the tip and a cell being analyzed is sufficient to deform the cell.

In FIGS. 3A and B, the difference in contact area for lipid vesicles on non-treated and hydrolyzed coverslips is shown. A strong interaction in many cases reflects a smaller interfacial distance. Besides positive effects on seal resistance, a strong interaction also increases the stability of the attachment, since more energy is needed to free the lipid membrane from the contact surface. A number of strategies may be implemented to achieve a highly hydrophilic surface. In one aspect, a glass (i.e., $SiO_2$) surface is made more hydrophilic in comparison with its native state by hydrolyzing the surface using an RCA-1 cleaning step, for example, by immersing the surface in a 70-80° C. solution of water, hydrogen peroxide and ammonia ($H_2O:H_2O_2:NH_3$ 5:1:1) for 10 minutes, followed by rinsing in deionized water, or by flame-treating the surface, or by coating the surface with a highly charged polymer.

(3) The Affects of Fluid Flow on the Formation of a High Electrical Resistance Seal The addition of an extra force (e.g., produced by a streaming fluid) when initially sealing a cell membrane against a surface, shifts the force equilibria of the system. This produces a new energy minima and can bring the system over a local energy maxima to a new minima. By exposing a cell membrane which is loosely attached to a surface defining an opening which separates the cell membrane from a electrode compartment, to a liquid flow of controlled velocity and directionality, the cell membrane can be stabilized to increase the resistance of the seal between the cell membrane and the surface.

The effects of liquid flow on a patch-clamped cell arise from the force (Stokes drag) exerted by the flow on the cell. This force can be calculated from the following equation:

$$F = 6\pi r \eta v$$

where F is the force, r, the radius of the cell, v, the velocity of the fluid and η, the viscosity of the fluid. This relationship is valid for low Reynold's number flow and for spherical particles.

A flow rate of 2 mm/s past a 5-μm-radius spherical cell in an aqueous medium with a viscosity of 1 centipoise will result in a force of ~200 pN. In comparison, the sedimentation force acting on the same cell is ~0.4 pN.

Although the discussion below emphasizes pressure-driven flow owing to its simplicity of implementation, a number of appropriate means can be designed for transporting liquids in microchannels, including but not limited to, electro-osmotic flow, surface-tension driven flow, moving-wall driven flow, thermo-gradient driven flow, ultrasound-induced flow, and shear-driven flow. These techniques are known in the art and are also described in U.S. Provisional Application Ser. No. 60/356,377, filed Feb. 12, 2002, the entirety of which is incorporated by reference herein.

The ability to record ion channel activities for prolonged periods of times using patch clamp, critically depends on the stability and high electrical seal resistance of the cell-substrate interface. Here, the improved stability of the "giga seal" under a range of flow conditions is described. There are also other considerations, in particular, impaired cell viability caused by run down of intracellular systems and metabolites, as well as receptor desensitization, that need to be considered when cells are used for very long recording times. However, for many receptor and ion channel systems, these factors play only a minor role and patch clamp recordings can be performed for many hours with a single cell using the system and methods of the invention.

In addition to the importance of surface treatment and optimized opening geometry, the results below demonstrate that a pushing force produced by a head-on fluid flow, effectively pushing the cell towards a surface defining an opening, can greatly stabilize the seal between the cell and the surface, allowing measurements of the electrical properties of the cell, (e.g., such as patch clamp recordings), to be performed for prolonged periods of time with increased high seal resistance.

Systems, System Components, and Methods for Increasing the Efficiency of a Patch Clamp Recording Device In one aspect, the invention provides systems, system components, and methods for performing measurements of the electrical properties of a cell membrane for prolonged periods of time, e.g., greater than about 20 minutes, preferably greater than about one hour, greater than about 2 hours, greater than about 3 hours, greater than about 4 hours, or greater than about 5 hours.

In one aspect, a system according to the invention comprises an electrode compartment comprising one or more electrodes, a lumen for receiving an electrolyte solution and for electrically coupling the electrode(s) to a cell membrane, and a surface defining an opening that is in fluid communication with the lumen. In one aspect, the lumen is the hollow portion of a patch clamp micropipette. In another aspect, the lumen is part of a cell chamber for receiving a cell membrane in an on-chip patch clamp device, such as a patch clamp array device. Preferably, the cell membrane is in electrical communication with the electrodes through contact with the electrolyte solution.

As used herein, the electrode(s) and lumen comprising electrolyte solution define an "electrode compartment." In some instances the electrical elements can form part of the electrode compartment. The surface defining the opening in communication with the lumen serves as a partition between the electrode compartment and cell, and more particularly, between the electrode compartment, and a bath solution in which the cell membrane resides.

Suitable surfaces include glass (e.g., when the surface is part of a patch clamp micropipette) or a polymer such as a carbon-based polymer, a silicone-based polymer, a plastic, and modified or treated forms thereof.

Preferably, the surface defining the opening is non-planar, and more preferably, is protruding. When the surface defining the opening comprises an aperture of an on-chip device, preferably, the surface topography at the aperture is also protruded such that the opening is in a different plane from the remainder of the insulating surface forming the device, and preferably, is higher than the remainder of the insulating surface by at least about 1 µm-1000 µm., and preferably, by at least about 1-100 µm. Generally, the size of the protrusion is selected to be large enough to create stress on a cell surface.

Alternatively, or additionally, the surface is treated so as to render at least the cell membrane-contacting portions of the surface hydrophilic, e.g., such as by an RCA cleaning method, or by flame-treating, or by chemical treatment, as described above.

Alternatively, or additionally, surface features at the opening may be modified to enhance the formation of a high electrical resistance seal. For example, cells have been shown to arrange, interact with, and react to, nanoscale structures such as reeves, columns, rods, and protrusions in surfaces and these interactions have been demonstrated to be important for cell motility, positioning and ability to attach to surfaces. Thus, nanostructured surfaces are likely to be important in the sealing process and to provide stable seals for long-term recordings. Nanostructures can be generated on surfaces for separating a cell from an electrode compartment using methods known in the art, such as by hard or soft lithography, vapor deposition, or by Atomic Force Microscopy (AFM).

In another preferred aspect, in an on chip device, such as a patch clamp array device, the surface topography of the cell chamber itself is designed to maximize the seal between a cell membrane and the opening of the cell chamber. In one aspect, the chamber comprises a non-planar surface feature that restricts the movement of the cell within the chamber and/or helps to position the cell relative to the surface defining the opening, to increase the electrical resistance of the seal between the cell and cell-contacting surface (see, e.g., FIG. 4 and FIG. 6). For example, a pyramidal structure can be microfabricated at the base of the cell chamber. In one aspect, the tip of the pyramidal structure is recessed so as to receive a cell.

Preferably, the cell chamber is relatively shallow. As used herein, the term "shallow" refers to the fact that a cell is constrained within the chamber from moving freely within the chamber and therefore does not substantially change its position within the chamber, i.e., the cell will move less than about two times the diameter of the cell-contacting surface of a sensor for delivering current to the cell. Fluid flow in this instance may be provided through the use of microchannels in communication with the cell, but which do not otherwise provide their contents to the portion of the cell chamber that comprises the electrolyte solution. One or more fluidic channels and/or valves can be incorporated into the device of the present invention in order to permit fast solution exchange (i.e., perfusion) of the cell membrane.

In an on chip device, such a patch clamp array device, a cell membrane is preferably placed in proximity to the surface comprising the opening. The addition of the cells to individual chambers of an array device, can be mediated by dispensing them, e.g., such as by using nQUAD aspirate dispensers. Other methods can used to position a cell such as electrophoresis, suction, the use of voltage pulses, and the like.

In one aspect, pressure-driven flow is used to manipulate the movement of cells from microfluidic channels in a substrate to an appropriate cell chamber of an on chip patch clamp device. Routing of cells can be affected by blocking a branch of a channel in a substrate comprising a plurality of microchannels, using valves as are known in the art, thereby moving the cells along with bulk solution flow into another, selected channel.

Additionally, or alternatively, electroosmosis can be used to produce motion in a stream containing ions, e.g., such as buffer solution, by application of a voltage differential or charge gradient between two or more electrodes. Neutral (uncharged) cells can be carried by the stream. See, e.g., as described in U.S. Published Application No. 20020049389.

Dielectrophoresis is believed to produce movement of dielectric objects, which have no net charge, but have regions that are positively or negatively charged in relation to each other. Alternating, non-homogeneous electric fields in the presence of cells cause the cells to become electrically polarized and thus to experience dielectrophoretic forces. Depending on the dielectric polarizability of the particles and the suspending medium, dielectric particles will move either toward the regions of high field strength or low field strength. The polarizability of living cells depends on the type of cell and this may provide a basis for cell separation, e.g., by differential dielectrophoretic forces. See, e.g., as described in U.S. Published Application 20020058332.

Radiation pressure can also be used to deflect and move cells with focused beams of light such as lasers or optical tweezers.

In another aspect, the system is part of a cell-based biosensor such as is described in U.S. Provisional Application 60/356,377, filed Feb. 12, 2002, the entirety of which is incorporated by reference herein. In this aspect, a cell, or portion thereof, is placed within a cell containing receptacle or reservoir and is exposed to a bath solution. The cell-containing receptacle is preferably an open volume compartment comprising a base and walls that can receive fluid from one or more fluid sources in communication with the open volume compartment. The biosensor comprises an electrode compartment that can be brought into proximity to the cell by moving the cell, the chamber or the electrode compartment. The cell chamber may be part of a microfluidic device comprising a plurality of microchannels to provide fluid streams, reagents, and/or the cells themselves to the cell chamber. One or more cells can be routed into the cell chamber from channels using one or more of the methods described above, i.e., pressure-driven flow, electroosmosis, dielectrophoresis, radiation pressure (e.g., optical tweezers), and the like.

The exact geometry of the cell chamber is not limiting, so long as it is able to support a cell or portion thereof, or a plurality of cells or portions thereof, in proximity to at least one electrode compartment, such as a patch clamp micropipette. In this aspect, the chamber typically comprises a bath solution that is physiologically compatible with an intact cell. The at least one electrode compartment (e.g., micropipette) comprises an electrolyte solution for maintaining suitable electrical communication between a cell membrane and an electrode within the electrode compartment. The cell is separated from the electrode compartment by a surface defining an opening through which the electrolyte solution can flow, electrically coupling the cell to the one or more electrodes in the electrode compartment.

The cell can be moved in proximity to the electrode compartment using fluid flow. One or more fluid streams in the open volume chamber may be created through the use of microchannels feeding into the open volume chamber as is described in U.S. Provisional Application Ser. No. 60/356,377 and can be used to provide a pushing force on the cell. Alternatively, or additionally, a cell can be moved using optical tweezers or by moving the electrode compartment itself (e.g., through the used of a micropositioner, such as when the electrode compartment comprises a patch clamp micropipette). The cell chamber itself can be configured to include one or more electrical elements for creating an electrical field to aid in positioning cell(s) in proximity to an appropriate electrode compartment, e.g., to create electroosmotic flow within the cell chamber or to polarize a cell to facilitate its movement towards an electrode compartment.

Fluid flow also can be used to increase the electrical resistance of a seal between a cell membrane and a surface defining an opening that separates the cell from an electrode compartment. For example, a cell, loosely attached at the opening of the surface, can be placed in proximity the outlet of a fluid flow source providing a liquid stream. While the cell is exposed to the flow, the area of cell membrane that contacts the surface defining the opening increases dramatically creating a stable seal (See, e.g., Example 3 and figures).

Accordingly, in one aspect, a cell membrane is placed in sufficient proximity to a fluid stream to receive pressure from the stream. This pressure facilitates formation of, or enhances, a seal between a cell membrane and the opening of the surface that separates the cell membrane from an electrode compartment. The fluid stream may be provided to a chamber comprising a cell, such as an open volume chamber in a cell-based biosensor, as described above. In an on chip patch clamp device, the fluid stream may be provided to a cell through microfluidic channels microfabricated in the device using methods routine in the art.

Preferably, the fluid flow source provides a liquid stream with a fluid velocity ranging from 0.01 mm/s to 100 cm/s, preferably, 0.1 mm/s to 10 cm/s.

Figure 11A:
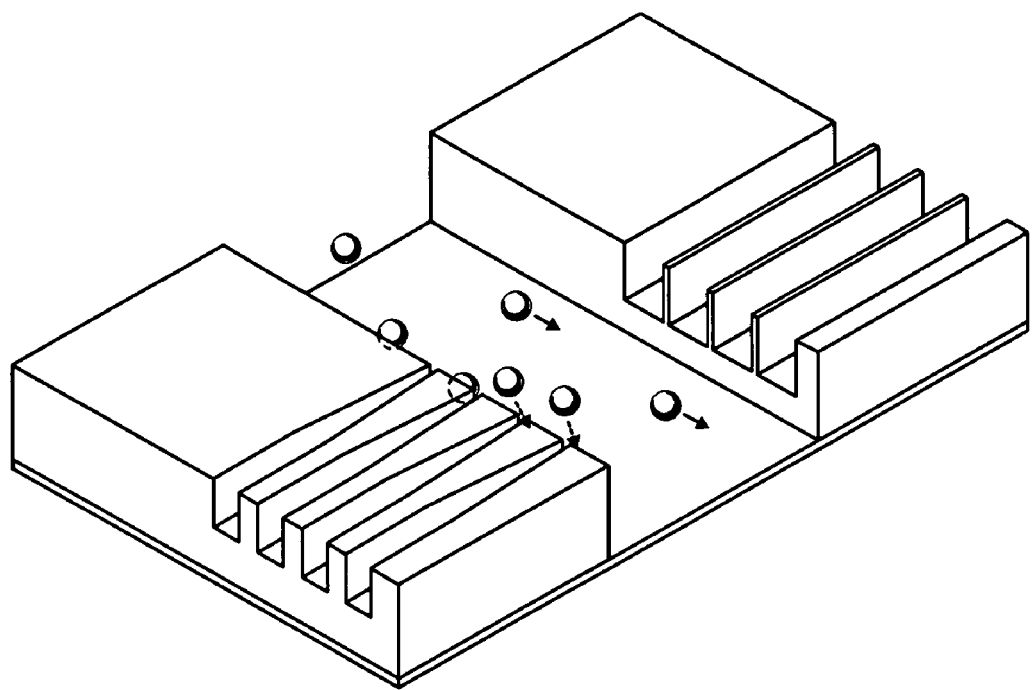
FIGS. 11A-B are schematic diagrams showing a cell-based biosensor for automatically positioning cells at a plurality of nonplanar elements, which are an integral part of a microfluidic chip, using two sets of fluid streams flowing perpendicularly to each other. The cells move at an angle to the plane comprising the plurality of tip openings.

Accordingly, in one aspect, the invention provides, a cell-based biosensor having a fluid flow source comprising at least one outlet entering a chamber or reservoir for containing one or more cells. The fluid flow source can comprise at least one microchannel capable of providing a fluid stream to one or more cells (see, e.g., FIGS. 2A and B, and FIGS. 10A and B). In another aspect, the fluid flow source comprises a plurality of outlets for providing a plurality of fluid streams to position and/or maintain the position of one or more cells relative to a micropipette tip. The plurality of outlets may lie in a single plane or in multiple planes, e.g., such as in the form of a stack of microchannels on a substrate (not shown). Multiple fluid flow sources can be provided as part of a single substrate providing fluid streams which flow in different directions, i.e., such as perpendicular to each other (see, e.g., FIGS. 11A and B) to enable a cell to be moved at an angle relative to the plane of the cell-contacting surface. Additional configurations of fluid flow sources are disclosed in U.S. Provisional Application 60/356,377, filed Feb. 12, 2002, the entirety of which is incorporated by reference herein.

In addition to the methods described above for forming high electrical resistance seals, a suction can applied at the opening of the surface separating the cell from the electrode compartment to enhance the electrical resistance of the seal. Alternatively, or additionally, one or several voltage pulses are applied at the opening to increase the electrical resistance of the seal (e.g., using the internal electrode of a micropipette or the one or more electrodes of a patch clamp array).

The sequence described above is illustrated in FIG. 7, for example.

Alternatively, the sequence of events can be the following:
A surface comprising an opening for separating a cell membrane from an electrode compartment is positioned close to a cell membrane by either moving the cell membrane, by moving the surface, or by moving both the cell membrane and the surface. A small suction and/or one to several voltage pulses are applied at the opening.

A cell membrane, loosely held at the surface (e.g., less than 0.01 μm from the surface), is placed in proximity to the outlet of a fluid flow source that provides a liquid stream. While the cell membrane is exposed to the flow stream, the surface area of the membrane in contact with the surface increases dramatically, creating a stable seal. After a predetermined time or when a satisfactory electrical reading of resistance is reached, the cell is taken out of the flow stream, whereupon more suction or more voltages are applied to at the surface until a suitable recording configuration is achieved, i.e., one which does not vary significantly over multiple sequential readings.

Figure 8:
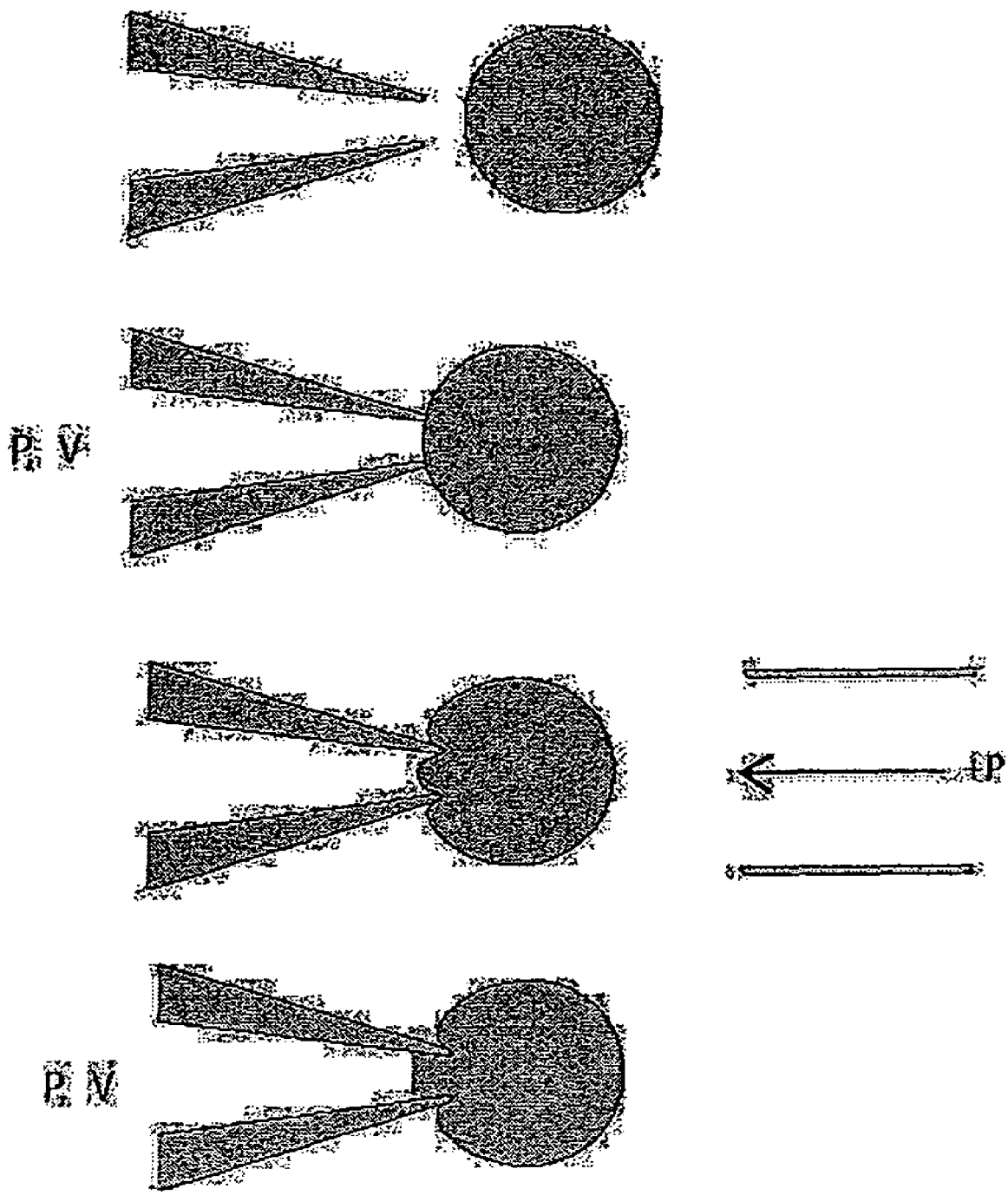
FIG. 8 is a schematic diagram illustrating a method for obtaining a tight seals in a patch clamp device using suction pressure/electric fields under fluid flow conditions according to another aspect of the invention. The arrow in the Figure shows the direction of fluid flow from a single fluid flow source and a sequence of events in which the electrical resistance of a seal between a cell and a surface is increased by placing the cell in proximity to a fluid stream.

The sequence described above is illustrated in FIG. 8.

Figure 9:
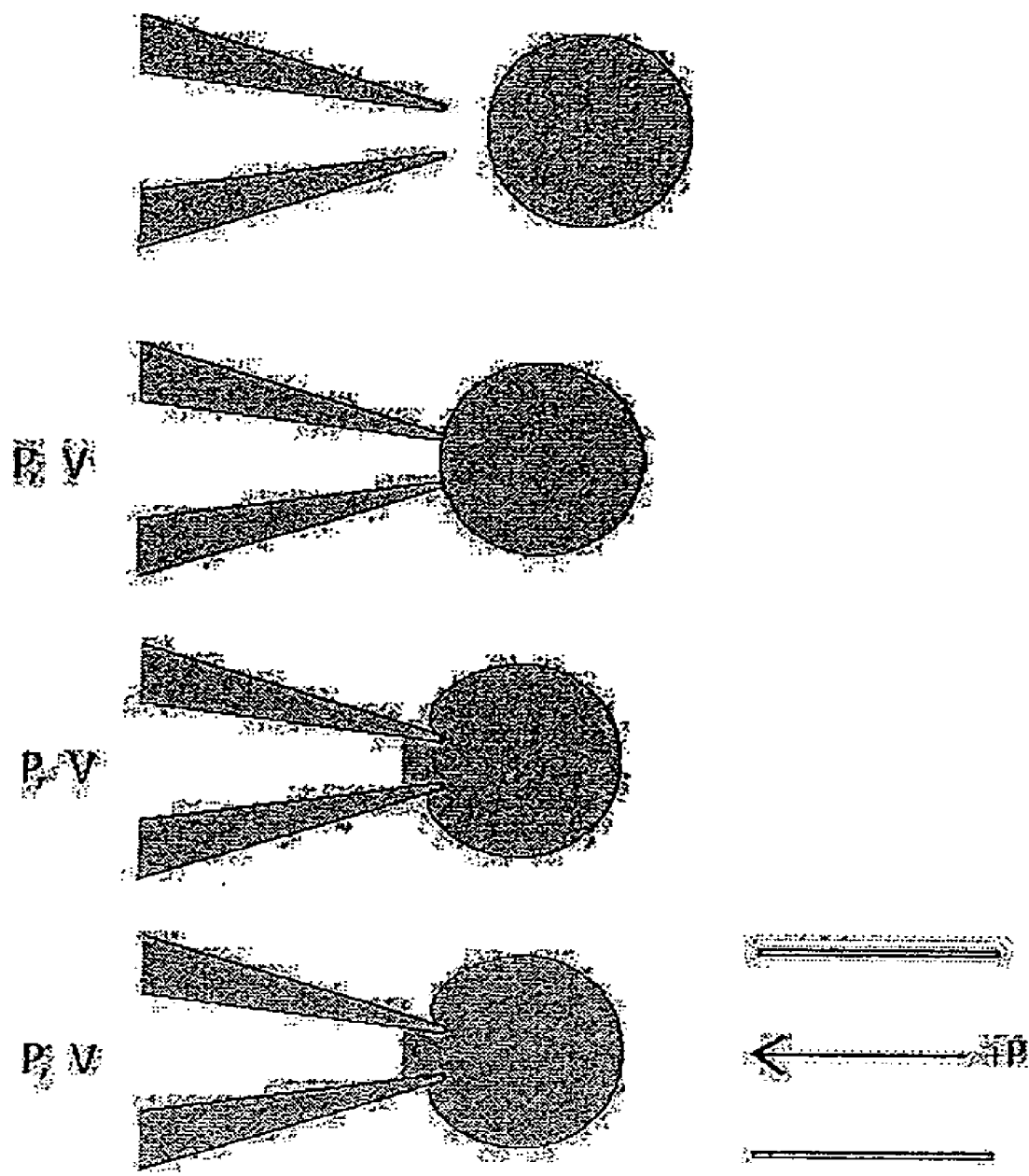
FIG. 9 is a schematic diagram illustrating a method for obtaining a tight seal between a cell and the surface of a patch clamp device using suction pressure/electric fields under fluid flow conditions to establish a high electrical resistance seal.

Alternatively, the sequence of events can be the following. A surface for separating a cell from an electrode compartment is positioned close to a cell and/or a cell is positioned close to the surface. A suction is applied at the surface and/or one or several voltage pulses are applied at the surface until a suitable cell recording configuration is reached. In one preferred aspect, the cell held at the cell-contacting surface is placed in proximity to a liquid stream until a desired electrical resistance is obtained. This sequence is shown in FIG. 9.

Figure 6:
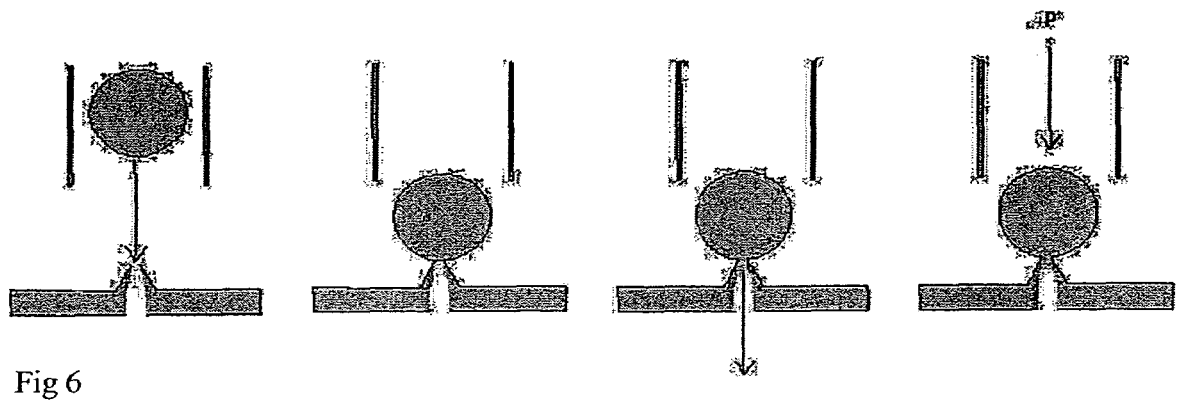
FIG. 6 is a schematic diagram illustrating a method of the invention in which fluid flow is used to establish and/or maintain a high resistance seal between a cell and the opening of a cell chamber in an on-chip patch clamp device. A cross section through a side of such a device is shown. The cell is indicated as a sphere, while the insulating surface of the device is indicated as a grey, generally planar structure comprising a microfabricated protruding opening (only the portion of the cell chamber communicating with the opening is shown). Fluid flow is provided from a fluid source (indicated as vertical parallel lines in the Figure). Contact between the cell and an electrolyte solution in the cell chamber couples the cell to one or more electrodes of the device (not shown), establishing electrical communication between the electrode(s) and cell. Exploiting the drag force exerted on a cell by fluid flow, either a pressure suction or a small electric pulse (0.01 V-10V) is used to establish electrical contact between cellular interior and the electrolyte solution. The stages of this process are shown from left to right in the Figure. The seal is further stabilized with constant applied pressure (P) on the patched cell created by the fluid flow (shown at the right side of the Figure).
Figure 7A:
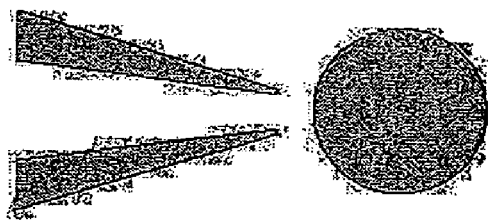
FIGS. 7A-D illustrate a method according to one aspect of the invention for obtaining tight seals in patch clamp using suction pressure (P) or electric fields (V) under fluid flow conditions.
Figure 7B:
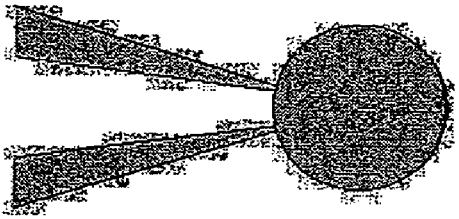
Figure 7C:
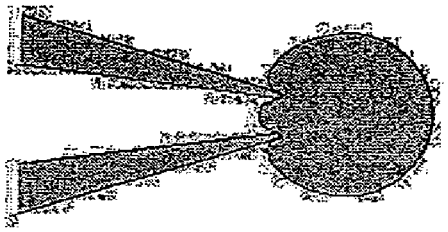
Figure 7D:
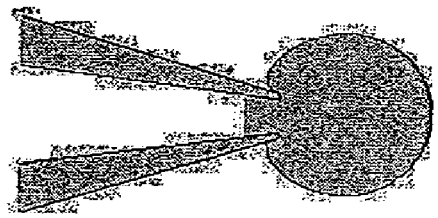
Figure 11B:
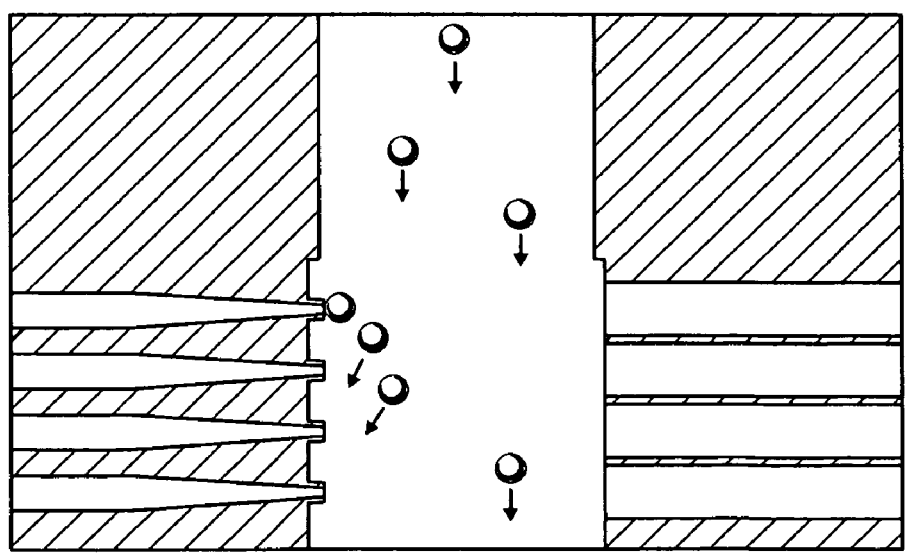

FIG. 6 shows an example of an embodiment where a cell is guided to a protruded surface defining an opening for separating a cell from an electrode compartment in a patch clamp array device. A flow stream normal to the generally planar portion of the insulating surface is provided to exert a pushing force on the cell. Where the device comprises multiple electrode compartments, cells can further be automatically positioned at a plurality of openings to such compartments by moving cells in a stream at an angle greater than or lesser than 90° to the base surface (FIG. 10) or perpendicular to this plane (FIG. 11). A suction pressure and/or voltage is then applied at the openings such that the cells are attracted or drawn to the openings of respective electrode compartments. Alternatively, dielectrophoresis can be used as known in the art or other alternating current (ac) methods, as described above.

The systems described above can be used in any method that generally comprises determining the electrical properties of one or more cell membranes. Suitable cells or portions thereof for use in the method include, but are not limited to, bacterial, yeast, insect, and cells. For example, *Bacillus* spp., *Escherichia coli, Streptococcus* spp., *Streptomyces* spp., *Pseudomonas* spp. can be used. Yeast cells such as *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytic*, as well as other lower eukarotes, also can be used.

Insect cell lines may also be used, including, but not limited to, *Aedes aegypti, Autographa californica, Bombyx mori, Drosophila melanogaster, Spodoptera frugiperda*, and *Trichoplusia ni*.

Mammalian cell lines include, but are not limited to immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells NIH/3T3, 293 cells (ATCC #CRL 1573), COS-7, 293, BHK, CHO, TM4, CV1, VERO-76, HELA, MDCK, BRL 3A, W138, Hep G2, MMT 060562, TRI cells, as well as others. A well-known example of an avian cell line is the chicken B cell line "DT-40".

Specific animal cells include, but are not limited to, leukemia L1210 cells (In Modern Pharmacology, pp. 1121-1129 (1978)); guinea pig heart cells (Journal of Physiology 397: 237-258 (1988); starfish egg cells (The Journal of General Physiology 70:269-281 (1977) and denervated frog muscle fibers (Neher et al., *Nature* 260 (Apr. 29, 1976).

Cells analyzed using the systems and methods of the invention include cells that have been transfected to express recombinant gene products. For example, cells can be engineered to express particular ion channels by transfecting such cells with appropriate cDNAs (see, e.g., U.S. Pat. No. 5,670,335).

As discussed above, artificial cells or vesicles also can be used with/or without recombinantly made proteins inserted into the membranes of such cells. See, e.g., U.S. Pat. Nos. 5,795,782 and 6,022,720.

Accordingly, in one aspect, a system comprising a surface defining an opening which separates a cell membrane from an electrode compartment is provided and the cell membrane is placed in sufficient proximity to the opening and exposed to conditions in which a high electrically resistant seal forms with between the cell membrane and the surface (e.g., a resistance of at least about 1 Gohm). In one aspect, the surface defining the opening is non-planar, preferably protruded. Alternatively, or additionally, the surface is hydrophilic. In one aspect, fluid flow is used to position the cell membrane in seal forming proximity to the surface defining the opening. Alternatively, or additionally, fluid flow is used to maximize the electrical resistance of a seal already formed. Preferably, at least one measurement of an electrical property of the cell membrane is obtained such as a voltage or current across the cell membrane. More preferably, electrical propert(ies) are measured as the cell is responding to, or after a cell has responded to, a condition and/or agent in a bath solution surrounding the cell.

Examples of agents, include, but are not limited to, proteins, DNA, RNA, PNA, receptor agonists, receptor antagonists, neurotransmitter, neurotransmitter analogues, enzyme inhibitors, ion channel modulators, G-protein coupled receptor modulators, transport inhibitors, hormones, peptides, toxins, antibodies, pharmaceutical agents, chemicals, purinergics, cholinergics, serotonergics, dopaminergics, anesthetics, benzodiazepines, barbiturates, steroids, alcohols, metal cations, cannabinoids, cholecystokinins, cytokines, excitatory amino acids, GABAergics, gangliosides, histaminergics, melatonins, neuropeptides, neurotoxins, endothelins, NO compounds, opioids, sigma receptor ligands, somatostatins, tachykinins, angiotensins, bombesins, bradykinins, prostaglandins and combinations thereof.

A search for genes encoding ion channels or transporter proteins can be carried out by parallel transfection of cells with genes to be tested, followed by screening for ionic currents as described herein.

The systems described herein may also be useful for screening compound libraries, to characterizations the pharmacological properties of compounds, and to obtain dose-response data.

Examples of agents that may be used for the apparatus and methods of the invention include drugs, receptor agonists, receptor antagonists, neurotransmitter, neurotransmitter analogues, enzyme inhibitors, ion channel modulators, G-protein coupled receptor modulators, transport inhibitors, hormones, peptides, toxins, antibodies, pharmaceutical agents, chemicals and combinations of these agents. Specific agents which may be used for the systems and methods of the invention include purinergics, cholinergics, serotonergics, dopaminergics, anesthetics, benzodiazepines, barbiturates, steroids, alcohols, metal cations, cannabinoids, cholecystokinins, cytokines, excitatory amino acids, GABAergics, gangliosides, histaminergics, melatonins, neuropeptides, neurotoxins, endothelins, NO compounds, opioids, sigma receptor ligands, somatostatins, tachykinins, angiotensins, bombesins, bradykinins, prostaglandins and combinations of these agents.

EXAMPLES

The invention will now be further illustrated with reference to the following examples. It will be appreciated that what follows is by way of example only and that modifications to detail may be made while still falling within the scope of the invention.

Example 1

Fabrication of Chip-Based Protruded Structure that Mimics the Geometry of a Patch-Clamp Micropipette A number of methods exist to microfabricate protruded cell contact surfaces having suitable geometries for carrying out patch-clamp measurements. Here, one particular procedure is described, by which a circular opening at the tip of a pyramidal structure in a cell chamber is microfabricated.

Masks for photolithography were produced using standard e-beam writing on a JEOL JBX-5DII electron beam lithography system (medium reflective 4" chrome masks and Shipley UV5 resists, 50 keV acc. voltage, dose 15 $\mu C/cm^{-2}$, exposure current 5 nA). The resist was spin coated at 2000 rpm for 60 s giving 250 nm of resist and soft baked for 10 minutes at 130° C. on a hotplate before exposure. The pattern was post exposure baked for 20 minutes in an oven at 130° C. and developed for 60 s in Shipley MF24-A, rinsed in DI water and ashed in a reactive ion etcher (Plasmatherm RIE m-95, 30 s, 50 W, 250 mTorr, 10 ccm $O_2$). The chrome was etched for 1-2 minutes in Balzers' chrome etch #4. The mask was stripped of the remaining resist using Shipley 1165 remover and rinsed in acetone, isopropanol and DI water. A 3", [100], low N-doped Silicon wafers polished on two sides with 700 nm of thermally grown silicon dioxide and a total thickness of 380 μm were cleaned in a reactive ion etcher (Plasmatherm RIE m-95 (30 s, 50 W, 250 mTorr, 10 ccm $O_2$)), spin coated with Shipley S-1813 photoresist at 4000 rpm, giving 1.3 μm of resist, and exposed through mask No. 1 for a dose of 110 mJ/cm$^2$ at 400 nm wavelength on a Carl Süss MA6 mask aligner. The unit cell of pattern No. 1 consisted of 450-500 μm squares, where the quality and thickness of the wafer determined size of the square (see, e.g., FIG. 4A).

Figure 4A:
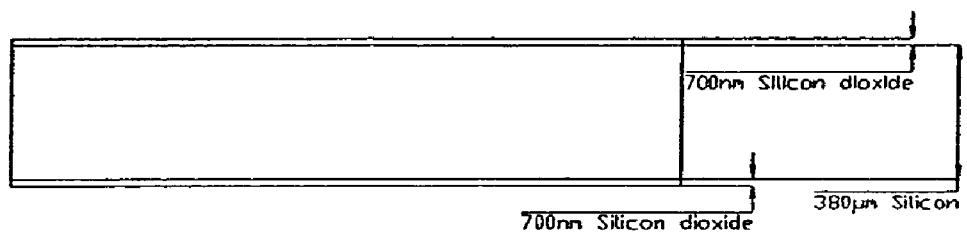
Figure 4B:
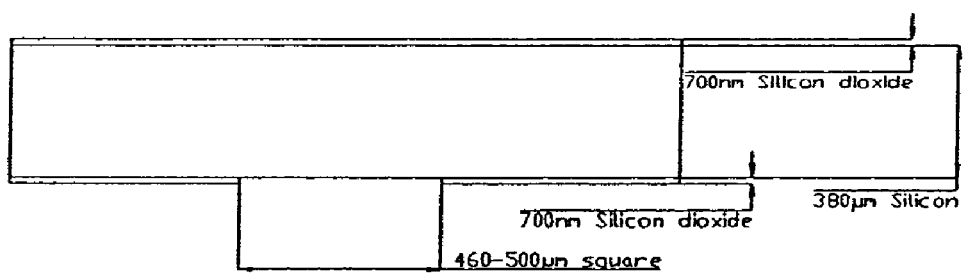
Figure 4C:
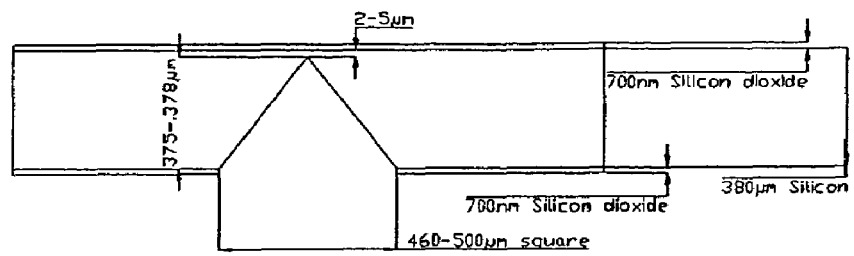
Figure 4D:
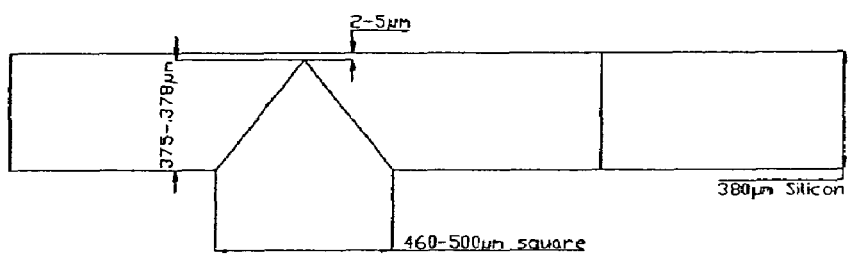

The wafer was developed for 45 s in Shipley MF319, rinsed in DI water, and ashed in a reactive ion etcher (Plasmatherm RIE m-95, 30 s, 50 W, 250 mTorr, 10 ccm $O_2$). The wafer was finally hard baked for 10 minutes at 130° C. The other side of the wafer was coated with S-1813 resist in the same manner and immediately hard baked for 10 minutes at 130° C. The silicon dioxide was etched with SioTech buffered oxide etch for 12-14 minutes rinsed in DI water. The wafer was stripped of the remaining resist with acetone, rinsed in isopropanol and DI water (FIG. 4B). The wafer was immersed in a bath of anisotropic enchant (an aqueous solution of 25% tetramethylammonium hydroxide) and etched for approximately 9.5 hours at 90° C. (FIG. 4C). The etching rate was typically 0.65 μm×min$^{-1}$ and the anisotropy 40:1. The wafers was stripped of the remaining Silicon dioxide and immersed in RCA-1 (a 1:1:5 mixture of NH$_3$:H$_2$O$_2$:H$_2$O at 75° C.) for 10 minutes, in 2% HF for 10 minutes, and in RCA-2 (a 1:1:5 mixture of HCl:H$_2$O$_2$:H$_2$O at 80° C.) for 10 minutes.

Figure 4E:
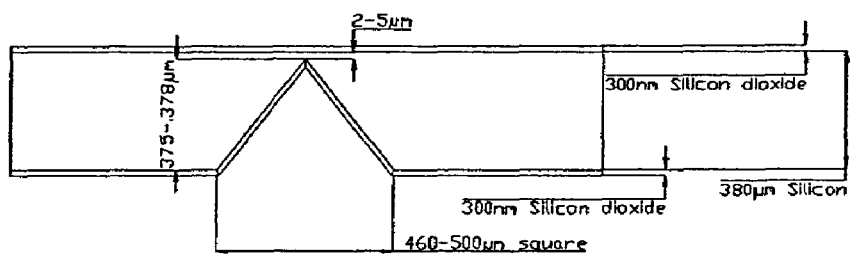
Figure 4F:
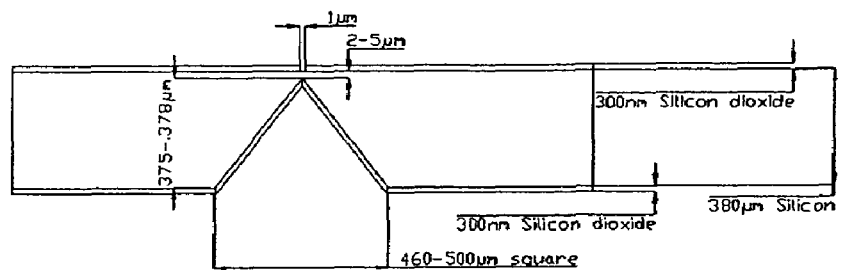
Figure 4G:
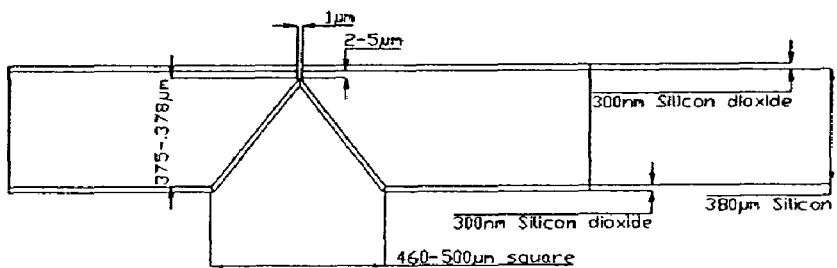
Figure 4H:
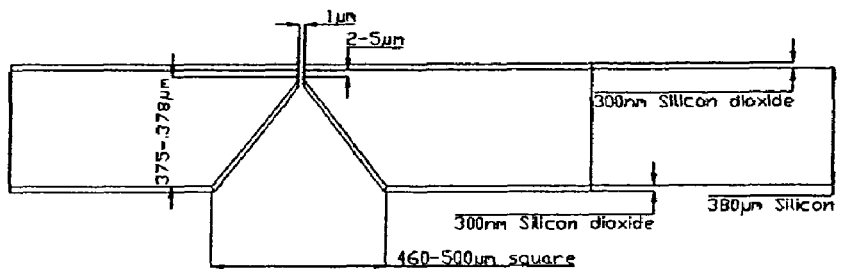

The wafer was finally rinsed with DI water in a combined rinse- and dryer. The wafer was oxidized thermally at 1050° C. for 25 minutes yielding about 300 nm of Silicon dioxide (FIG. 4E). The unpatterned side of the wafer was spin coated with Shipley S-1813 photoresist at 4000 rpm, giving 1.3 μm of resist, and exposed through mask No. 2 (the unit cell of pattern No. 2 consisted in a 1 μm circle) for a dose of 110 mJ/cm$^{-2}$ at 400 nm wavelength on a Carl Süss MA6 mask aligner. The wafer was developed for 45 s in Shipley MF319 rinsed in DI water and ashed in a reactive ion etcher (Plasmatherm RIE m-95, 30 s, 50 W, 250 mTorr, 10 ccm O$_2$) (FIG. 4F). The Silicon dioxide was etched in the same system (Plasmatherm RIE m-95, 15 minutes, 100 W, 100 mTorr, 32 ccm CF$_4$, 8 ccm H$_2$, 1 ccm O$_2$) (FIG. 4G). The exposed Silicon was etched in a STS Multiplex deep reactive ion etcher using SF$_6$ as etching gas and C$_4$F$_8$ as passivation gas operating at 800 W of RF power, at a constant APC angle of 68% and the etching time was 7 s with an overrun time of 0.5 s, and the passivation time 4 s with an overrun time of 1 second. The pattern was etched until it reached the pyramidal Silicon dioxide structure buried in the Silicon (FIG. 4G). The exposed Silicon dioxide in the bottom of the aperture was etched a reactive ion etcher (Plasmatherm RIE m-95, 30 minutes, 100 W, 100 mTorr, 32 ccm CF$_4$, 8 ccm H$_2$, 1 ccm O$_2$) producing an aperture in the top of the pyramidal structure (FIG. 4H).

The wafer was once again exposed, this time through mask No. 3 (the unit cell of pattern No. 3 consisted in a 50 μm circle), for a dose of 110 mJ/cm$^{-2}$ at 400 nm wavelength on a Carl Süss MA6 mask aligner. The wafer was developed for 45 seconds in Shipley MF319, rinsed in DI water, and ashed in a reactive ion etcher (Plasmatherm RIE m-95, 30 s, 50 W, 250 mTorr, 10 ccm O$_2$) (FIG. 4I). The Silicon dioxide was etched in the same system (Plasmatherm RIE m-95, 15 minutes, 100 W, 100 mTorr, 32 ccm CF$_4$, 8 ccm H$_2$, 1 ccm O$_2$). The structure was finally released by etching away the silicon around it in a STS Multiplex deep reactive ion etcher using SF$_6$ as etching gas and C$_4$F$_8$ as passivation gas operating at 800 W of RF power, at a constant APC angle of 68% and the etching time was 7 seconds with an overrun time of 0.5 seconds, and the passivation time 4 seconds with an overrun time of 1 seconds.

The pattern was etched until 5-10 μm of the structure was visible (FIG. 4J). The wafer was stripped of the remaining resist with acetone, rinsed in isopropanol and DI water and ashed in a reactive ion etcher (Plasmatherm RIE m-95, 30 s, 50 W, 250 mTorr, 10 ccm O$_2$). FIGS. 4L and 4L show the SEM images of the resulting microfabricated structure.

Example 2

Liposome Adhesion to Flame Treated and Hydrolyzed Surface in Comparison with Regular Glass Surface To investigate how the surface properties of a substrate affected lipid membrane adhesion we used giant unilamellar liposomes prepared with a dehydration/rehydration technique as model system. Free liposomes under no external stresses can be thought of as fluctuating bags, with fixed areas, whose shapes are decided only by their minimum bending energies, given by $$E_D = \frac{1}{2}k_c \int (c_1 + c_2 - c_0)^2 dS + k'_c \int c_1 c_2 dS$$

where $c_1$ and $c_2$ are the principal curvatures, $c_0$ is the spontaneous curvature arising from the preferred molecular packing of the lipid molecules, and $k_c$ and $k'_c$ are the elastic bending modulus and saddle splay modulus, respectively. When treating vesicles with a fixed spherical topology, the gaussian term (second term at the right side in equation) can be neglected. Giant unilamellar vesicles provide a useful control model for studying the interactions between the lipid membrane and the chemically modified surfaces.

If a vesicle adheres to a substrate the contribution from surface interactions must be included in the equation. Adhered vesicles are no longer tension free, and lateral membrane tension due to area expansion must also take into account. Since, due to the electrostatic shielding of the water, all colloidal forces are very short range they can be approximated to act solely at the liposome-solid interface. Gathering these forces into one contact potential, φ, the adhesive contribution to the free energy of a vesicle can be written as $$E_\kappa = -\phi A^*,$$

where $A^*$ is the contact area of the bound part of the vesicle membrane.

Because of the Brownian motion of a flaccid membrane surface, the contact area of an adhering liposome will grow progressively until it reaches its equilibrium. The surface free energy of a bound vesicle will then be given by the balance between the adhesive forces, lateral tension and bending rigidity;

$$E_D = \frac{1}{2}k_c \int (c_1 + c_2 - c_0)^2 dS + k'_c \int c_1 c_2 dS - \phi A^*$$

Consequently, the shape of a bound vesicle reflects the strength of adhesion in the system. At low contact potentials a bound vesicle is largely spherical with a very small contact area, this type of vesicle-substrate interaction is commonly denoted as the weak adhesion regime. As the contact potential increases, a vesicle will interact more strongly with the substrate surface, and appears as truncated spheres or dome-like shapes. This type of interaction is often referred to as the "strong adhesion regime." If the contact potential is very high, the adhesive forces in the system may lead to tension-induced vesicle lysis that for lipid vesicles typically occurs at lateral membrane tensions of 4-10 mN/m. In this case, the vesicle will rupture and spread onto the substrate.

To use liposomes as model systems for systematically studying the strength of lipid membrane adhesion onto chemically modified surface, the following procedures were used:

Liposome Preparations

To make fluorescently labeled unilamellar liposomes, a dehydration/rehydration technique was used. Lipids (100 mg/ml) and a fluorescent membrane dye (DiO 0.5 mg/ml) were dissolved in chloroform as stock solution. The dehydration/rehydration method described by Criado and Keller was used with modifications[2]. Briefly, 5 μl of lipid dispersion (1 mg/ml) was placed on a coverslip and the solution was then dehydrated in a vacuum dessicator at 4° C. The lipid film was partially dehydrated, and then carefully rehydrated with PBS buffer (Trizma base 5 mM, $K_3PO_4$ 30 mM, $KH_2PO_4$ 30 mM, $MgSO_4$ 1 mM, EDTA 0.5 mM, pH 7.8). After a few minutes giant unilamellar liposomes started to form.

Microscopy and Micromanipulation

All experiments were performed on an inverted microscope (Leica DM IRB, Wetzlar, Germany) equipped with a Leica PL Fluotar 40× objective and a water hydraulic micromanipulation system (high graduation manipulator: Narishige MWH-3, Tokyo, coarse manipulator: Narishige MC-35A, Tokyo). The liposomes were manipulated by using micromanipulator controlled carbon fiber microelectrodes (5 μm diameter, Dagan Corp., Minneapolis, Minn., U.S.A.) as tweezers.

Fluorescence imaging was achieved by sending the output of an $Ar^+$-laser (Spectra-Physics 2025-05, 488 nm) through a 488-nm line interference filter, followed by a spinning disc to break the coherence and scatter the laser light. The laser light was collected by a lens and was sent through a fluorescein filter (Leica I-3) into the objective (Leica PL Fluotar, 40×) to excite the fluorescent dyes. The fluorescence was collected by the objective and a CCD-camera (C2400-41H, Hamamatsu Photonics K.K., Japan) controlled by an Argus-20 image processor (Hamamatsu Photonics Norden AB, Solna, Sweden) was used to capture the images. Recordings were made using a SuperVHS (Panasonic S-VHS AG-5700, Stockholm, Sweden, 25 Hz frame collection rate). The same camera set-up was also used for differential interference contrast imaging. Digital image editing was performed using the Argus-20 system and Adobe premiere and photoshop graphic software.

Surface Modifications

The borosilicate cover slips (24×60×0.17 mm, Knittel Gläser, Germany) used for the experiments were surface modified using the RCA-1 cleaning Protocol. In brief, the coverslips were boiled for 10 minutes in a solution of deionized water, hydrogen peroxide, and ammonia ($H_2O:H_2O_2:NH_3$ 5:1:1, 75° C.) followed by rinsing in deionized water. As a reference surface, borosilicate coverslips cleaned by rinsing in ethanol followed by immense rinsing in deionized water were used. The coverslips were used immediately after the surface treatment/cleaning.

Chemicals

Chloroform, EDTA (titriplex III), magnesium sulfate, and potassium dihydrogen phosphate were from Merck (Darmstadt, Germany). Trizma base, potassium phosphate, soybean lecithin (Type II-S) were from Sigma (St. Louis, Mo.). DiO (3,3'-dioctadecyloxacarbocyanine perchlorate), were from Molecular Probes (Leiden, Netherlands). Glycerol was from J. T. Baker and deionized water from a Milli-Q system (Millipore Corporation, Bedford, Mass.) was used.

The liposomes used for these experiments were prepared from soybean lechitin (SBL) which is a heterogeneous mixture consisting of phosphatidylcholine (45.7%), phosphatidylethanolamine (22.1%), phosphatidylinositol (18.4%), phosphatidic acid (6.9%) and others (6.9%) (Polar lipid extract composition from Avanti Polar Lipids, Inc.). The SBL lipids have a negative net charge with a zeta potential of about −120 mV. The substrates used in this example were naked borosilicate coverslips washed with deionized water and ethanol (reference substrate), or RCA-1 surface modified borosilicate coverslips. The effect of the RCA-1 treatment is to increase the hydrophillicity of the surface of the borosilicate substrate.

As can be seen in the fluorescence micrographs in FIG. 3B, liposomes immobilized onto the reference substrate, appears as virtually intact spheres, indicating that the vesicle-substrate interaction was in the weak adhesion regime. When liposomes were placed on RCA-1 treated borosilicate substrates, the vesicle-substrate interaction was much stronger and the surface immobilized vesicles appeared as flattened hemispheres (FIG. 3C). This experiment thus reveals that membrane adhesion is much stronger on the surface modified substrate. Consequently, the surface modification of the borosilicate substrate resulted in a significant increase of the effective contact potential between the SBL membrane and the borosilicate surface. This effect is extremely important for obtaining and maintaining high resistance seals in a planar patch clamp cell-contacting surface. The seal resistance is dramatically increased with the appropriate surface treatment.

Example 3

Stabilization of Patch-Clamp Seal Using Fluid Flow

Microchannels were molded in a polymer, polydimethylsiloxane (PDMS), which were then sealed irreversibly onto a glass coverslip to form an enclosed channel having four walls.

The procedure used is the following:

(1) A master used for molding PDMS was fabricated by first cleaning the wafer to ensure good adhesion to the photoresist, followed by spin coating a layer (~50 μm) of negative photoresist (SU 8-50) onto the wafer. This layer of negative photoresist was then soft baked to evaporate the solvents contained in the photoresist. Photolithography with a mask aligner was carried out using a photomask having the appropriate patterns that were prepared using e-beam writing. The exposed wafer was then baked and developed by washing away the unexposed photoresist in an appropriate developer (e.g. propylene glycol methyl ether acetate).

(2) This developed wafer (master) was surface passivated by silanizing in vacuo with a few hundred microliters of tridecafluoro-1,1,2,2-tetrahydrooctyl-1-trichlorosilane for a few hours.

(3) Degassed PDMS prepolymer was poured on top of the silicon master and left in an oven to cure at 60° C. for two hours.

(4) The cured PDMS mold containing the microchannel features was then sealed irreversibly to a glass substrate after oxidization in an oxygen plasma for ~1 min. Channel dimensions used in this example were approximately 100 μm wide and 50 μm deep.

The experiments described here used a simple single-channel structure. This microchannel was interfaced to a polyethylene tubing by first punching a smooth hole through the PDMS with a sharp hole-puncher having the appropriate dimensions. Polyethylene tubing having an outer diameter slightly greater the punched hole was inserted into the hole, and the tubing formed a pressure seal owing to the elastomeric nature of PDMS. The polyethylene tubing was connected to a syringe needle having the appropriate size (gauge), which was connected to a syringe. Controlled pressure for driving fluid flow was accomplished with a high precision syringe pump (CMA/100, Microinjection pump, Carnegei Medicin).

Patch clamp experiments were carried out in the whole-cell configuration. The pipettes for whole-cell recording were fabricated from thick-walled borosilicate glass capillaries having an outer diameter of 1.5 mm and an inner diameter of 0.86 mm (Harvard Apparatus LTD Edenbridge, Kent, UK). The diameters and the resistances of the tips were ~2.5 μM and 5-15 MΩ, respectively. The estimated series resistance was always <50 MΩ and holding potentials were corrected for voltage errors due to series resistance. The patch clamp electrode solution contained 100-mM KCl, 2-mM MgCl$_2$, 1-mM CaCl$_2$, 11-mM EGTA, and 10-mM HEPES; pH was adjusted to 7.2 with KOH. All experiments were performed at room temperature (18-22° C.).

Signals were recorded with an Axopatch 200 A (Axon inc. California, U.S.A) patch-clamp amplifier, at a holding potential of −70 mV, and were digitized and stored on a computer hard drive (sample frequency 10 kHz, filter frequency 200 Hz using a 8 pole Bessel filter) and analyzed using a PC and Clampfit 8.1 software (Axon, Inc.). The experimental chamber containing the microchannel structure was mounted on an inverted microscope stage equipped with 40× and 10× objectives (Nikon, Japan). Mounted to the microscope was a CCD camera (Hamamatsu) connected to a video for recording of the scan rates, the sampling rate for the video was 25 Hz. This equipment together with micromanipulators (Narishigi, Japan) was placed on a vibration-isolated table inside a Faraday cage. The patch clamp amplifier, the Digidata board, filters, the video and PCs, were kept outside the cage to minimize interference from line frequency.

Adherent PC-12 cells were cultivated on circular cover slips in Petrie dishes for 2-6 days (DMEM/F 12 medium supplemented with antibiotics and antimyocotin (0.2%), fetal calf serum (10%), and L-glutamine). Before the patch clamp experiments, cells were washed and detached in a HEPES-saline buffer, containing (in mM): 10 HEPES, 140 NaCl, 5 KCl, 1 CaCl$_2$, 1 MgCl$_2$, 10 D-glucose (pH 7.4), and placed in an open buffer reservoir at the outlet of the microchannel.

The fluid streams leaving the outlets of the channels exert a drag force on the patched cell which can be calculated from $F=6\pi r\eta v$, where F is the force, r, the radius of the cell, v, the velocity of the fluid and η, the viscosity of the fluid. A flow rate of 2 mm/s past a 5-μm-radius spherical cell in an aqueous medium with a viscosity of 1 centipoise will result in a force of ~200 pN. In comparison, the sedimentation force acting on the same cell is ~0.4 pN. It was found that this force, pushing the cell towards the seating surface of the pipette, effectively stabilizes the cell-pipette seal allowing patch-clamp measurements to be performed for prolonged periods of time. For example, cells could be routinely kept in a whole-cell configuration in excess of 40 minutes and sometimes as long as 110 minutes. This is an improvement compared to stability times observed in traditional patch-clamp systems with a free-hanging cell under no applied external forces, which typically is in the range of 10-20 minutes. This increased mechanical seal stability also results in increased electrical seal resistances, as illustrated in FIG. 5.

To obtain the measurements shown in FIG. 5, fluid flow was driven by pressurized air and PC-12 cells were patched clamped in the whole cell configuration and placed in the HBS flow at about ~25 μm from the channel outlet. A flow rate of 3 mm/s was used and the cell was held at a fixed position relative to the channel. Increases in resistance were calculated for ten cells and the average increase was 56%±24%. The seal resistance increase was independent of the strength of the seal before exposure to the fluid stream. The seal increase was calculated from the difference in leakage current before and after the cell was placed in the flow.

Variations, modifications, and other implementations of what is described herein will occur to those of ordinary skill in the art without departing from the spirit and scope of the invention.

All of the references, patents, patent publications and international applications cited herein are incorporated by reference herein in their entireties.

What is claimed is:

1. A microfluidic chip having a length, width and height, wherein said height is the smallest dimension, said microfluidic chip comprising:
    a) a cell chamber having at least one nonplanar element for establishing and/or maintaining electrical communication with a cell, wherein said nonplanar element has a surface defining an opening for separating a cell from an electrode compartment and is an integral part of the microfluidic chip, and wherein the surface defining the opening comprises portions of a wall of said cell chamber;
    b) a first channel lateral to and in communication with said cell chamber, and oriented so as to provide a fluid flow with respect to the non-planar element so as to exert a positive fluidic pressure on a cell attached to the surface defining the opening of the non-planar element; and
    c) a second channel lateral to said cell chamber and in communication with the surface defining the opening on the wall of the cell chamber so as to produce a negative pressure on a cell drawing it into contact with the surface defining the opening,
    wherein said cell chamber, said first channel and said second channel each comprise two walls and a base wherein the walls are parallel to the height of said microfluidic chip and the base is perpendicular to the height of said microfluidic chip, and whereby a high electrical resistance seal is established and/or maintained between a cell and the surface defining the opening by the combination of the positive pressure of the fluid flow from the first channel and the negative pressure from the second channel.

2. The microfluidic chip of claim 1, wherein the at least one nonplanar element comprises a raised portion having an opening in which a conducting fluid is disposed.

3. The microfluidic chip of claim 2, wherein the conducting fluid is in electrical communication with a conducting element.

4. The microfluidic chip of claim 1, wherein at least a portion of the nonplanar element comprises a conducting surface.

5. The microfluidic chip of claim 1, wherein the nonplanar element comprises a nonconducting surface.

6. The microfluidic chip of claim 1, wherein at least a portion of the substrate comprises a polymer.

7. The microfluidic chip of claim 6, wherein the polymer comprises an elastomeric polymer.

8. The microfluidic chip of claim 1, wherein at least a portion of the nonplanar element comprises a carbon material.

9. The microfluidic chip of claim 1, wherein the surface is protruding or rounded.

10. The microfluidic chip of claim 9, wherein the protruding surface is one or more of a column, rod, or reeve.

11. The microfluidic chip of claim 1 or 2, further comprising a voltage source for creating an electrically resistant seal between a surface of the nonplanar element defining the opening and a cell in proximity to the opening.

12. The microfluidic chip of claim 11, wherein the resistance of the seal is at least about 100 Mohm.

13. The microfluidic chip of claim 1, wherein the nonplanar element is pyramidal, conical, elliptical, toroidal, or comprises stacked planar elements.

14. The microfluidic chip of claim 1, wherein the cell chamber comprises a plurality of the nonplanar elements.

15. The microfluidic chip of claim 1, wherein at least a portion of a surface of the nonplanar element is hydrophilic.

16. The microfluidic chip of claim 1, further comprising a fluid controlling mechanism to control hydrostatic pressure of at least one channel.

17. The microfluidic chip of claim 1, wherein a surface of the nonplanar element is modified by exposure to chemical washing.

18. The microfluidic chip of claim 1, wherein a surface of the non-planar element is modified by gas phase chemical deposition.

* * * * *

(12) INTER PARTES REEXAMINATION CERTIFICATE (527th)
United States Patent
Karlsson et al.

(10) Number: US 7,390,650 C1
(45) Certificate Issued: Feb. 11, 2013

(54) SYSTEM AND METHOD FOR OBTAINING AND MAINTAINING HIGH-RESISTANCE SEALS IN PATCH CLAMP RECORDINGS

(75) Inventors: Mattias Karlsson, Göteborg (SE); Owe Orwar, Hovås (SE); Daniel T. Chiu, Seattle, WA (US); Jon Sinclair, Göteborg (SE); Kent Jardemark, Gothenburg (SE); Jessica Olofsson, Gothenburg (SE); Johan Pihl, Gothenburg (SE); Cecilia Farre, Vastra Frolulnda (SE)

(73) Assignee: Cellectricon AB, Gothenburg (SE)

Reexamination Request:
No. 95/000,549, Jun. 9, 2010

Reexamination Certificate for:
Patent No.: 7,390,650
Issued: Jun. 24, 2008
Appl. No.: 10/645,834
Filed: Aug. 20, 2003

Related U.S. Application Data

(60) Provisional application No. 60/404,886, filed on Aug. 21, 2002.

(51) Int. Cl.
*C12M 1/34* (2006.01)
*G01N 27/327* (2006.01)

(52) U.S. Cl. ............... 435/287.1; 204/403.1; 422/82.02; 435/285.2; 435/288.5

(58) Field of Classification Search .................. None
See application file for complete search history.

(56) References Cited

To view the complete listing of prior art documents cited during the proceeding for Reexamination Control Number 95/000,549, please refer to the USPTO's public Patent Application Information Retrieval (PAIR) system under the Display References tab.

*Primary Examiner* — Krisanne Jastrzab

(57) ABSTRACT

The invention provides a system, system components, and a method for rapidly obtaining and stably maintaining a cell in optimal contact with the cell-contacting surface of a sensor in a cell-based biosensor. In one aspect, the system maximizes the seal between a whole cell and the cell-contact surface of a patch clamp micropipette, maximizing the efficiency of a whole cell patch clamp recording.

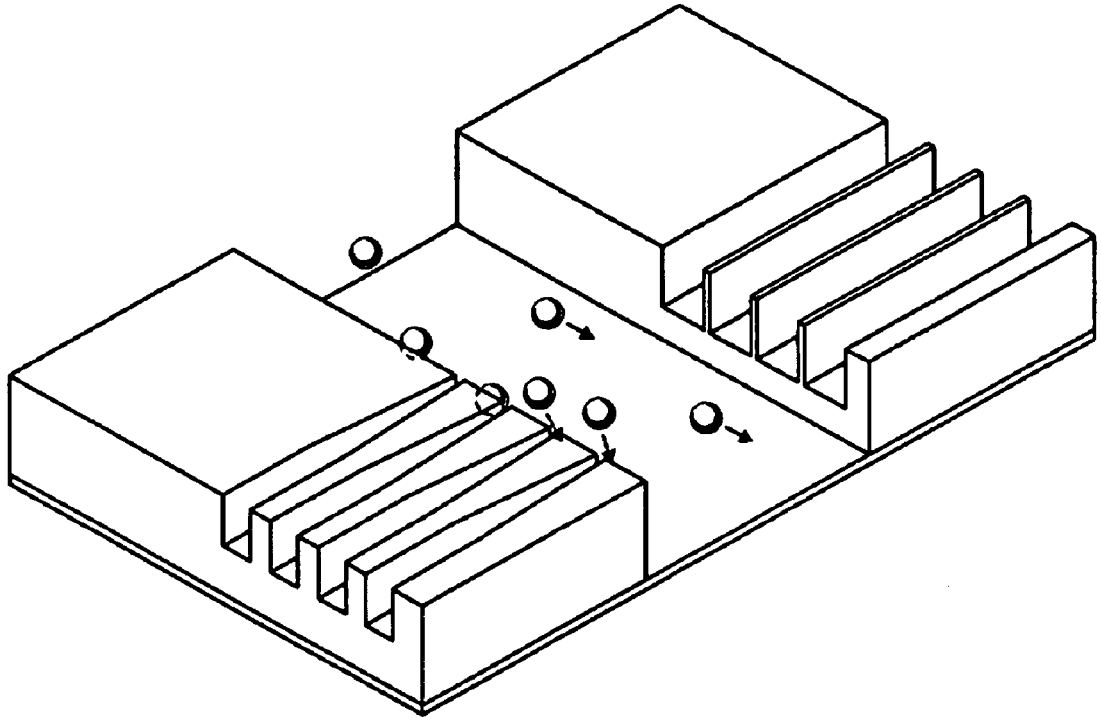

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1, 5-9 and 11-17 are cancelled.

Claims 2-4, 10 and 18 were not reexamined.

\* \* \* \* \*